US008168165B2

(12) United States Patent
Brate et al.

(10) Patent No.: US 8,168,165 B2
(45) Date of Patent: May 1, 2012

(54) ALKYLATED INTERLEUKIN-18 COMPOSITIONS

(75) Inventors: Elaine Marie Brate, Grayslake, IL (US); Tracey D. Rae, Glenview, IL (US); Cheng Zhao, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 6 days.

(21) Appl. No.: 12/643,898

(22) Filed: Dec. 21, 2009

(65) Prior Publication Data

US 2010/0166702 A1 Jul. 1, 2010

Related U.S. Application Data

(60) Provisional application No. 61/140,258, filed on Dec. 23, 2008, provisional application No. 61/147,061, filed on Jan. 23, 2009.

(51) Int. Cl.
*A61K 45/00* (2006.01)
*A61K 49/14* (2006.01)

(52) U.S. Cl. .................. 424/85.2; 424/9.1; 435/69.52

(58) Field of Classification Search .................. None
See application file for complete search history.

(56) References Cited

U.S. PATENT DOCUMENTS

| | | | |
|---|---|---|---|
| 5,006,309 A | 4/1991 | Khalil et al. | |
| 5,063,081 A | 11/1991 | Cozzette et al. | |
| 5,089,424 A | 2/1992 | Khalil et al. | |
| 5,294,404 A | 3/1994 | Grandone et al. | |
| 5,795,784 A | 8/1998 | Arnquist et al. | |
| 5,856,194 A | 1/1999 | Arnquist et al. | |
| 6,420,141 B1 * | 7/2002 | Zagury et al. | 435/69.7 |
| 6,582,689 B1 | 6/2003 | Johnson | |
| 6,706,487 B1 | 3/2004 | Abdel-Meguid et al. | |
| 6,896,880 B2 | 5/2005 | Gillispie et al. | |
| 7,041,479 B2 | 5/2006 | Swartz et al. | |
| 7,060,299 B2 * | 6/2006 | Alavattam et al. | 424/491 |
| 7,311,902 B2 * | 12/2007 | Bam et al. | 424/85.2 |
| 2003/0170881 A1 | 9/2003 | Davis et al. | |
| 2004/0018577 A1 | 1/2004 | Campbell et al. | |
| 2004/0038332 A1 | 2/2004 | Swartz et al. | |
| 2005/0054078 A1 | 3/2005 | Miller et al. | |
| 2005/0147610 A1 | 7/2005 | Ghayur et al. | |
| 2006/0110389 A1 | 5/2006 | Nishida et al. | |
| 2006/0160164 A1 | 7/2006 | Miller et al. | |

FOREIGN PATENT DOCUMENTS

| | | |
|---|---|---|
| EP | 767178 A1 | 4/1997 |
| EP | 692536 B1 | 11/2000 |
| EP | 712931 B1 | 2/2001 |
| EP | 712931 B2 | 2/2001 |
| WO | WO9724441 A1 | 7/1997 |
| WO | WO0158956 A2 | 8/2001 |
| WO | WO02074250 A2 | 9/2002 |
| WO | WO2003057821 A2 | 7/2003 |
| WO | WO2004091517 A2 | 10/2004 |

OTHER PUBLICATIONS

Dawson et al., Mono Alkylating Agents as Therapeutic Agents in Plasma Sterilization and Plasma Protein Stabilization, J. Surgical research 2, 31-35,1962.*
Bickley J.F., et al., "Reactions of Some Cyclopentenones With Selected Cysteine Derivatives and Biological Activities of the Product Thioethers," Bioorganic & Medicinal Chemistry, 2004, vol. 12, pp. 3221-3227.
Co-pending U.S. Appl. No. 60/981,473, filed Oct. 19, 2007, and published Apr. 23, 2009 as PCT WO2009/052392.
Co-pending U.S. Appl. No. 61/142,048, filed Dec. 31, 2008, published Jul. 8, 2010 as PCT W02010/078443.
Di Gleria K., et al., "N-(2-Ferrocene-Ethyl)Maleimide : A New Electroactive Sulphydryl-Specific Reagent for Cysteine-Containing Peptides and Proteins," FEBS Letters, 1996, vol. 390 (2), pp. 142-144.
International Preliminary Report on Patentability and Written Opinion for Application No. PCT/US2009/069318, mailed on Jun. 29, 2011, 6 pages.
International Search Report and Written Opinion for Application No. PCT/US2009/069318, mailed on Mar. 1, 2010, 12 pages.
Kawashima M., et al., "Increased Production of Interleukin-18 in Synovium from Patients With Rheumatoid," J. Educ. Inform. Rheumatology, 1997.
Kim D.M., et al., "Prolonging Cell-Free Protein Synthesis by Selective Reagent Additions," Biotechnology Progress, 2000, vol. 16 (3), pp. 385-390.
Kim D.M., et al., "Prolonging Cell-Free Protein Synthesis With a Novel ATP Regeneration System," Biotechnology and Bioengineering, 1999, vol. 66 (3), pp. 180-188.
Li A., et al., "Optimized Gene Synthesis and High Expression of Human Interleukin-18," Protein Expression and Purification, 2003, vol. 32 (1), pp. 110-118.
Liu B., et al., "Production of a Biologically Active Human Interleukin 18 Requires its Prior Synthesis as PRO-IL-18," Cytokine, 2000, vol. 12 (10), pp. 1519-1525.
Matsumoto K., et al., "Elevated Interleukin-18 Levels in the Urine of Nephrotic Patients," Nephron, 2001, vol. 88 (4), pp. 334-339.
Noren C.J., et al., "A General Method for Jite-Specific Incorporation of Unnatural Amino Acid into Proteins," Science, 1989, vol. 244 (4901), pp. 182-188.
Okamura H., et al., "Cloning of a New Cytokine that Induces IFN-Gamma Production by T Cells," Nature, 1995, vol. 378 (6552), pp. 88-91.
Parikh C.R., et al., "Urinary IL-18 is an Early Predictive Biomarker of Acute Kidney Injury After Cardiac Surgery," Kidney International, 2006, vol. 70, pp. 199-203.

(Continued)

*Primary Examiner* — Elly-Gerald Stoica
(74) *Attorney, Agent, or Firm* — Audrey L. Bartnicki; Carol Larcher, Larcher & Chao Law Group

(57) ABSTRACT

Alkylated interleukin-18 (IL-18), compositions comprising alkylated IL-18, kits comprising such compositions, methods of alkylating IL-18, and methods of using compositions comprising alkylated IL-18.

16 Claims, No Drawings

OTHER PUBLICATIONS

Parikh C.R., et al., "Urine IL-18 is an Early Diagnostic Marker for Acute Kidney Injury and Predicts Mortality in the Intensive Care Unit," Journal of the American Society of Nephrology, 2005, vol. 16 (10), pp. 3046-3052.

Pei D.S., et al., "Cys74 and Cys163 are Necessary for IL-18 to elicit IFN- Production from Peripheral Blood Lymphoid Mononuclear Cells," Molecular Immunology, 2005, vol. 42 (11), pp. 1367-1373.

Ushio S., et al., "Cloning of the cDNA for Expression in Escherichia Activities of the Protein Human IFN-y-Inducing Factor, colj, and Studies on the Biologic Activities of the Protein," The Journal of Immunology, 1996, vol. 156, pp. 4274-4279.

Yamamoto Y., et al., "Generation of Highly Stable IL-18 Based on a Ligand Receptor Complex Structure," Biochemical and Biophysical Research Communications, 2004, vol. 317 (1), pp. 181-186.

* cited by examiner

ALKYLATED INTERLEUKIN-18 COMPOSITIONS

CROSS-REFERENCE TO RELATED APPLICATIONS

This application claims the priority U.S. Provisional Patent Application 61/147,061 filed Jan. 23, 2009 (pending), and U.S. Provisional Patent Application 61/140,258 filed Dec. 23, 2008 (pending), both of which are incorporated by reference in their entireties.

TECHNICAL FIELD

This disclosure relates to alkylated interleukin-18 (IL-18), compositions comprising alkylated IL-18, kits comprising such compositions, methods of alkylating IL-18, and methods of using compositions comprising alkylated IL-18.

BACKGROUND

IL-18 is a pro-inflammatory cytokine, which belongs to the IL-1 cytokine family, is synthesized as a 24 kD precursor requiring caspase-1 for cleavage into an active 18 kD molecule, and has potent biological activities. For example, it induces interferon-γ (IFN-γ) production by T-cells and splenocytes, and was initially referred to as interferon-γ-inducing factor (IGIF) (Okamura et al., Nature 378(6552): 88-91 (1995); and Ushio et al., J. Immunol. 156: 4274-4279 (1996)). It also enhances the killing activity of natural killer (NK) cells, promotes the differentiation of naïve CD4+ T-cells into Th1 cells, augments the production of granulocyte-macrophage colony-stimulating factor (GM-CSF), and decreases the production of interleukin-10 (IL-10). Thus, IL-18 plays a key role in many inflammatory diseases, including allergy and autoimmune diseases.

A mouse protein, which induces IFN-γ by immunocompetent cells, was disclosed by Kabushiki Kaisha Hayashibara Seibutsu Kayaku Kenkyujo ("Hayashibara"; Okayama-shi, Japan) in European Pat. App. No. 0692536 (the '536 EP application), which was published on Jan. 17, 1996. Certain physicochemical properties and a defined partial amino acid sequence were also disclosed in the '536 EP application, as were a protein having 157 amino acids (aa), two fragments thereof, DNA (471 base pairs (bp)) encoding the protein, hybridomas, protein purification methods, and methods for detecting the protein.

A human protein having 157 aa, as well as homologues thereof, and DNA encoding the protein were disclosed by Hayashibara in European Pat. App. No. 0712931 (the '931 EP application), which was published on May 22, 1996. Transformants, processes for preparing the protein, monoclonal antibodies against the protein, hybridomas, protein purification methods, and methods for detecting the protein were also disclosed.

A human protein, which has a specific 10-aa sequence near its N-terminus and which induces IFN-γ production by an immunocompetent cell, was disclosed by Hayashibara in European Pat. App. No. 0767178 (the '178 EP application), which was published on Apr. 9, 1997. Also disclosed were processes for producing the protein, and characterizations of the protein as a pharmaceutical agent, in particular an anti-oncotic or anti-tumor agent, an antiviral agent, an antibacterial agent, and an agent for the treatment of immunopathy and atopic diseases.

A precursor to IL-18 having 193 aa was disclosed by Incyte Pharmaceuticals, Inc., in Int'l Pat. App. No. WO 97/24441, which was published on Jul. 10, 1997. Also disclosed was the DNA encoding the precursor.

In addition to its potent biological activities, IL-18 has been determined to be a renal marker for various conditions or disease states, including, but not limited to, inflammatory disorders, e.g., allergy and autoimmune disease (Kawashima et al., J. Educ. Inform. Rheumatology 26 (2): 77 (1997)), acute kidney injury (Parikh et al., J. Am. Soc. Nephrol. 16: 3046-3052 (2005); and Parikh et al., Kidney Int'l 70: 199-203 (2006)), chronic kidney disease (such as when used as part of a panel assay), and minimal-change nephritic syndrome (MCNS) (Matsumoto et al., Nephron 88: 334-339 (2001)). Unfortunately, IL-18 is highly unstable at 37° C., and even at 22° C. (i.e., room temperature), especially in the absence of protein. This instability makes assaying for the presence or the level of IL-18 in a biological sample, such as urine, difficult due to the rapid loss of activity of IL-18 in control or calibrator compositions. Yamamoto et al. (Biochem. Biophys. Res. Comm. 317: 181-186 (2004)) has proposed replacing cysteine residues with serine in an effort to stabilize IL-18.

It is an object of the present disclosure to provide a more stable IL-18, which does not involve amino acid replacement. It is another object of the present disclosure to provide compositions comprising such an IL-18, as well as kits, and methods of making and using the IL-18. These and other objects, as well as inventive features, will become apparent from the detailed description provided herein.

SUMMARY

An isolated or purified, alkylated interleukin-18 (IL-18), in which at least one free sulfhydryl of a cysteine residue has been alkylated, is provided. Also provided is a composition comprising (i) an isolated or purified, alkylated IL-18, in which at least one free sulfhydryl of a cysteine residue has been alkylated, and (ii) a stabilizing protein. In this regard, the composition can comprise a known concentration of an isolated or purified, alkylated IL-18 and be a control/calibrator composition or part of a series of calibrating compositions. Accordingly, also provided is a series of calibrating compositions, which can be used in a method of determining the presence, amount or concentration of IL-18 in a sample. Each of the compositions in the series comprises (i) a known concentration of an isolated or purified, alkylated IL-18, in which at least one free sulfhydryl of a cysteine residue has been alkylated, and (ii) at least one stabilizing protein. Each of the compositions differs from the other compositions in the series by the concentration of alkylated IL-18.

A kit for assaying a test sample for IL-18 is also provided. The kit comprises at least one component for assaying the test sample for IL-18 and instructions for assaying the test sample for IL-18. The at least one component includes at least one composition comprising (i) a known amount of an isolated or purified, alkylated IL-18, in which at least one free sulfhydryl of a cysteine residue has been alkylated, and (ii) at least one stabilizing protein. If the kit comprises more than one composition, each of the compositions differs from the other compositions by the concentration of alkylated IL-18.

Further provided is an improved method of determining the presence, amount or concentration of IL-18 in a test sample by an immunoassay comprising comparing a signal generated by a detectably labeled antibody or a detectably labeled analyte as a direct or indirect indication of the concentration of IL-18 in the test sample to a signal generated as a direct or indirect indication of the concentration of IL-18 in a calibrator, which is optionally part of a series of calibrators in which each of the calibrators differs from the other calibrators in the series by the concentration of IL-18. The improvement comprises using a calibrator comprising (i) a known concentration of an isolated or purified, alkylated IL-18, in which at least one free sulfhydryl of a cysteine residue has been alkylated, and (ii) at least one stabilizing protein.

Still further provided is a method of alkylating an isolated or purified IL-18. The method comprises contacting the IL-18 with an alkylating agent under conditions that promote alkylation of the free sulfhydryls of the cysteine residues of the IL-18.

Even still further provided is a pharmaceutical composition comprising (i) a therapeutically or prophylactically effective amount of an alkylated IL-18, (ii) a pharmaceutically acceptable carrier, diluent, and/or excipient, and (iii) optionally, another active agent and/or an adjuvant, wherein the pharmaceutical composition is optionally part of a kit comprising one or more containers in which the alkylated IL-18, another active agent and/or the adjuvant can be present in the same or different containers. In this regard, also provided is a method of treating a patient in therapeutic or prophylactic need of IL-18. The method comprises administering to the patient a pharmaceutical composition comprising (i) a therapeutically or prophylactically effective amount of an alkylated IL-18, (ii) a pharmaceutically acceptable carrier, diluent, and/or excipient, and (iii) optionally, another active agent and/or an adjuvant.

DETAILED DESCRIPTION

The present disclosure is predicated, at least in part, on the discovery that interleukin-18 (IL-18) can be stabilized, such as at about 37° C., by alkylation of free sulfhydryls of cysteine residues present in the IL-18. The present disclosure is further predicated on the discovery that alkylated IL-18 can be further stabilized, such as at about 37° C., by a stabilizing protein.

Definitions

The following terms are relevant to the present disclosure.

(a) "About" refers to approximately a +/−10% variation from the stated value. It is to be understood that such a variation is always included in any given value provided herein, whether or not specific reference is made to it.

(b) "Alkyl group" as used herein means a straight- or branched-chain hydrocarbon containing from 1 to 10 carbon atoms, which is optionally substituted. Representative examples of alkyl groups include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl, carboxyamidomethyl, carbamidomethyl, carboxymethyl, and heteroatom alkyl groups, any of which can be substituted.

(c) "Alkylated" as used herein means that a hydrogen of at least one free sulfhydryl of at least one cysteine residue in any IL-18 is replaced with an alkyl group. By way of example, if an IL-18 comprises four cysteine residues, the free sulfhydryl in one, two, three or all four cysteine residues can be alkylated. By way of example, the hydrogen can be replaced with 3-4 carboxyamidomethyl.

(d) "Antibody" and "antibodies" refer to monoclonal antibodies, multispecific antibodies, human antibodies, humanized antibodies (fully or partially humanized), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies (e.g., dual variable domain antibodies, or DVD-IgGs), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_i$ and IgA$_2$), or subclass. An antibody, whose affinity (namely, $K_D$, $k_d$ or $k_a$) has been increased or improved via the screening of a combinatory antibody library that has been prepared using bio-display, is referred to as an "affinity matured antibody." For simplicity sake, an antibody against an analyte is frequently referred to herein as being either an "anti-analyte antibody," or merely an "analyte antibody" (e.g., an anti-IL-18 antibody or an IL-18 antibody).

(e) "Capping ratio" refers to the ratio of the number of alkylated cysteines to the total numbers of cysteines as calculated by mass spectrometry total peak area.

(f) "Component," "components," and "at least one component," refer generally to a capture antibody, a detection antibody, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine sample, in accordance with the methods described herein and other methods known in the art. Some components can be in solution or lyophilized for reconstitution for use in an assay.

(g) "Control" as used herein refers to a composition known to not contain alkylated IL-18 ("negative control") or to contain alkylated IL-18 ("positive control"). A positive control can comprise a known concentration of alkylated IL-18. "Control," "positive control," and "calibrator" may be used interchangeably herein to refer to a composition comprising a known concentration of alkylated IL-18 and a stabilizing protein. A "positive control" can be used to establish assay performance characteristics and is a useful indicator of the integrity of reagents (e.g., analytes).

(h) "CPSP acridinium ester" means 9-[N-tosyl-N-(3-carboxypropyl)]-10-(3-sulfopropyl)acridinium carboxamide.

(i) "IL-18" encompasses any IL-18, which is isolated or purified from a naturally occurring source, recombinantly produced, or synthesized and comprises at least one cysteine residue having a free sulfhydryl group.

(j) "Label" means a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein.

(k) "Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human.

(l) "Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). The present disclosure provides exemplary predetermined levels. However, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

(m) "Quality control reagents," in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

(n) "Sample," "test sample," and "patient sample" may be used interchangeably herein. The sample, such as a sample of urine, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

(o) "Series of calibrating compositions" is used herein to refer to a plurality of compositions comprising a known concentration of alkylated IL-18 and at least one stabilizing protein, wherein each of the compositions differs from the other compositions in the series by the concentration of alkylated IL-18.

(p) "SPSP acridinium ester" means N10-(3-sulfopropyl)-N-(3-sulfopropyl)-acridinium-9-carboxamide.

(q) "Stabilizing protein" encompasses any protein that has a stabilizing effect on a composition comprising an alkylated IL-18. By way of example, a stabilizing protein is a protein that stabilizes the activity (e.g., eliminates the loss of activity, delays the onset of loss of activity, slows the rate of loss of activity, or minimizes the loss of activity) of the alkylated IL-18 in the composition at about 37° C. for at least about 6 days, such as about 7 days, about 14 days, about 21 days or even about 31 days. "At least one stabilizing protein" is used herein to indicate that one or a combination of two or more stabilizing proteins can be included in a composition comprising an alkylated IL-18. In this regard, the composition can comprise a mixture of alkylated IL-18s, i.e., molecules of IL-18 that differ in terms of which or how many free sulfhydryls are alkylated.

(r) "Tracer" means an analyte or analyte fragment conjugated to a label, such as IL-18 conjugated to a fluorescein moiety, wherein the analyte conjugated to the label can effectively compete with the analyte for sites on an antibody specific for the analyte.

The above terminology is provided for the purpose of describing particular embodiments. The terminology is not intended to be limiting.

Alkylated IL-18

In view of the above, an isolated or purified, alkylated IL-18, in which at least one free sulfhydryl of a cysteine residue has been alkylated, is provided. Any IL-18 comprising at least one cysteine residue having a free sulfhydryl group can be alkylated. The IL-18 can be isolated or purified from a naturally occurring source, recombinantly produced, or synthesized in accordance with methods known in the art. Examples of IL-18 include those disclosed in the '536 EP application, the '931 EP application, and the '178 EP application. A recombinantly produced, human IL-18 (rhIL-18) is commercially available from Medical & Biological Laboratories Co., Ltd. (MBL; Japan). The hIL-18 is recombinantly expressed in $E.$ $coli.$ The IL-18 can be alkylated using any suitable method that results in replacement of a hydrogen of at least one free sulfhydryl of at least one cysteine residue with an alkyl group (as previously defined). By way of example, if an IL-18 comprises four cysteine residues, the free sulfhydryl in one, two, three or all four cysteine residues can be alkylated. By way of example, the hydrogen can be replaced with carboxyamidomethyl.

Preferably, the IL-18 is alkylated in accordance with the methods described herein. In the event that the IL-18 contains more than one cysteine residue having a free sulfhydryl, preferably more than one free sulfhydryl is alkylated. For example, if the IL-18 contains four cysteine residues, each of which has a free sulfhydryl, preferably at least one, more preferably at least two or three, and most preferably all four of the free sulfhydryls are alkylated. In this regard, alkylation in accordance with the methods described herein can result in a mixture of alkylated IL-18s, i.e., a mixture of IL-18s in which some have only one free sulfhydryl alkylated and others have two or more (depending on the number of free sulfhydryls) free sulfhydryls alkylated.

A preferred alkylated IL-18 is one in which at least one free sulfhydryl is alkylated with carboxyamidomethyl. Preferably, the alkylated IL-18 is alkylated rhIL-18, such as the one commercially available from MBL, in which at least one, more preferably at least two or three, and most preferably all four of the free sulfhydryls are alkylated. An example of a preferred alkylated IL-18, such as rhIL-18, is one alkylated with carboxyamidomethyl (via reaction with a sulfhydryl-reactive reagent comprising iodoacetamide) and having a capping ratio of about 2.5 to about 4.0 as determined by mass spectrometry. Alternatively, the alkylated IL-18 is one alkylated with carboxymethyl (via reaction with a sulfhydryl-reactive reagent comprising iodoacetic acid) or one alkylated via reaction with a sulfhydryl-reactive reagent comprising N-ethylmaleimide (NEM).

Alkylated IL-18 Compositions

Also provided is a composition comprising (i) an isolated or purified, alkylated IL-18, in which at least one free sulfhydryl of a cysteine residue has been alkylated, as described above, and (ii) at least one stabilizing protein. Any suitable stabilizing protein can be used in the composition, provided that it stabilizes the activity (e.g., eliminates the loss of activity, delays the onset of loss of activity, slows the rate of loss of activity, or minimizes the loss of activity) of the alkylated IL-18 in the composition at about 37° C. for at least about 6 days, such as about 7 days, about 14 days, about 21 days or even about 31 days. Examples of suitable stabilizing proteins include, but are not limited to, bovine serum albumin (BSA), human serum albumin (HSA), bovine γ-globulin (BGG), and/or Carnation® Instant Nonfat Dry Milk (Nestle U.S.A., Glendale, Calif.). A preferred stabilizing protein is BSA. Preferably, the stabilizing protein is present in the composition in an amount such that less than about 5% IL-18 activity is lost over six days at 37° C., less than about 6% IL-18 activity is lost over seven days at 37° C., less than about 11% IL-18 activity is lost over 14 days, less than about 15% IL-18 activity is lost over 15 days, or less than about 16% IL-18 activity is lost over 31 days. If BSA, HSA, BGG and/or Carnation® Instant Nonfat Dry Milk is used as the stabilizing protein, preferably the stabilizing protein is present in the composition in an amount from about 1% to about 5%, such as about 1%, about 2%, about 3%, about 4%, or about 5%, preferably in the absence of Proclin 300 (Sigma-Aldrich Co., St. Louis, Mo.). One or a combination of two or more stabilizing proteins can be included in a composition comprising an alkylated IL-18. In this regard, the composition can comprise a mixture of alkylated IL-18, i.e., molecules of IL-18 that differ in terms of which and/or how many free sulfhydryls are alkylated.

The composition can comprise a known amount of alkylated IL-18. When the composition comprises a known amount of alkylated IL-18, it can be used as a control, e.g., positive control, or a calibrator for a cutoff/predetermined level.

Also provided is a series of calibrating compositions, which can be used in a method of determining the presence, amount or concentration of IL-18 in a sample. Each of the compositions in the series comprises (i) a known concentration of an isolated or purified, alkylated IL-18, in which at least one free sulfhydryl of a cysteine residue has been alkylated, and (ii) at least one stabilizing protein, wherein each of the compositions differs from the other compositions in the series by the concentration of alkylated IL-18. For example, a series of calibrating compositions can comprise 0, about 25, about 75, about 250, about 600, and about 1,000 pg/mL of alkylated IL-18, respectively.

The concentration of an isolated or purified, alkylated IL-18 in a positive control, calibrator, or series of calibrators can be determined in accordance with assays known in the art. For example, the bicinchoninic (BCA) protein assay (Pierce Protein Research Products, Thermo Fisher Scientific Inc., Rockford, Ill.) can be used.

The compositions can comprise other components as are typically included in calibrator/control compositions. Examples of such components include buffers and salts.

IL-18 Antibodies

With regard to the methods of assay (and kit therefor), it may be possible to employ commercially available anti-IL-18 antibodies or methods for production of anti-IL-18 antibodies as described in the literature. These include, but are not limited to, those available from Santa Cruz Biotechnology Inc. (Santa Cruz, Calif.), GenWay Biotech, Inc. (San Diego, Calif.), and R&D Systems (RDS; Minneapolis, Minn.). Specific examples of monoclonal antibodies from RDS include the anti-human IL-18 monoclonal antibody 125-12H (catalog no. D044-3), the anti-human IL-18 monoclonal antibody 159-12B (catalog no. D045-3), and the anti-human IL-18 monoclonal antibody 25-2G (catalog no. D043-3). Other antibodies and portions thereof that bind to IL-18 are disclosed in Int'l Pat. App. Pub. No. WO 2001/058956, U.S. Pat. App. Pub. No. 2005/0147610, and U.S. Pat. No. 6,706,487. Optionally, such commercially available Abs are used as either capture or detection antibodies in assays that further include the antibodies as described herein. Likewise proprietary antibodies such as those of Abbott Laboratories (Abbott Park, Ill.) can be employed including but not limited to those described as anti-IL-18 mAbs 1-3392, 1-3458, 1-3750, 1-4060-110, 1-4091, and 1-4585-238, and other anti-IL-18 mAbs described in U.S. Pat. App. No. 61/147,062, filed Jan. 23, 2009, which is hereby incorporated by reference in its entirety for its teachings regarding same. These antibodies can be employed and combined in a variety of different configurations for capture and detection, such as would be adapted by one skilled in the art. Moreover, optionally one, two, three or more antibodies can be employed for capture, and/or likewise, for detection.

Kits

A kit for assaying a test sample for IL-18 is also provided. The kit comprises at least one component for assaying the test sample for IL-18 and instructions for assaying the test sample for IL-18. The at least one component includes at least one composition comprising (i) a known amount of an isolated or purified, alkylated IL-18, in which at least one free sulfhydryl of a cysteine residue has been alkylated, and (ii) at least one stabilizing protein. If the kit comprises more than one composition, each of the compositions differs from the other compositions by the concentration of alkylated IL-18.

The kit can comprise at least one component for assaying the test sample for IL-18 by immunoassay, e.g., chemiluminescent microparticle immunoassay, and instructions for assaying the test urine sample for IL-18 by immunoassay, e.g., chemiluminescent microparticle immunoassay. For example, the kit can comprise at least one capture antibody and/or at least one detection antibody. Alternatively or additionally, the kit can comprise a calibrator or control, e.g., isolated or purified, alkylated IL-18, such as alkylated rhIL-18, and/or at least one container (e.g., tube, microtiter plates or strips, which can be already coated with an anti-IL-18 mAb) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions can be in paper form or computer-readable form, such as a disk, CD, DVD, or the like.

Any antibodies, which are provided in the kit, such as recombinant antibodies specific for IL-18, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

The kit (or components thereof), as well as the method of determining the concentration of IL-18 in a test sample by an immunoassay as described below, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., analyte antibody or capture antibody) is attached (which can impact sandwich formation and analyte reactivity), and the length and timing of the capture, detection and/or any optional wash steps. Whereas a non-automated format, such as an ELISA, may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format, such as an ELISA, may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an IL-18 assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the second detection antibody labeled with alkaline phosphatase (or other label). Within the fluid pouch of the cartridge is an aqueous reagent that includes p-aminophenol phosphate.

In operation, a sample suspected of containing IL-18 is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody, IL-18, and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte IL-18 in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, microparticle diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-STAT® cartridge format, using a nucleic acid sequence linked to the signal antibody as a signal amplifier.

Furthermore, the methods and kits optionally are adapted for use on an automated or semi-automated system. Some of the differences between an automated or semi-automated system as compared to a non-automated system (e.g., ELISA) include the substrate to which the first specific binding partner (e.g., analyte antigen or capture antibody) is attached (which can impact sandwich formation and analyte reactivity), and the length and timing of the capture, detection and/or any optional wash steps. Whereas a non-automated format such as an ELISA may include a relatively longer incubation time with sample and capture reagent (e.g., about 2 hours) an automated or semi-automated format (e.g., ARCHITECT®) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Method of Assay

Also provided is an improvement to a method of determining the concentration of IL-18 in a test sample by an immunoassay comprising comparing a signal generated by a detectably labeled antibody or a detectably labeled analyte as a direct or indirect indication of the concentration of IL-18 in the test sample to a signal generated as a direct or indirect indication of the concentration of IL-18 in a calibrator, which is optionally part of a series of calibrators in which each of the calibrators differs from the other calibrators in the series by the concentration of IL-18. The improvement comprises using a calibrator comprising (i) a known concentration of an isolated or purified, alkylated IL-18, in which at least one free sulfhydryl of a cysteine residue has been alkylated, and (ii) at least one stabilizing protein. The at least one free sulfhydryl of a cysteine residue can be alkylated with carboxyamidomethyl (via reaction with a sulfhydryl-reactive reagent comprising iodoacetamide as described herein below), such as in a capping ratio of about 1 to about 4. Alternatively, the at least one free sulfhydryl of a cysteine residue can be alkylated with carboxymethyl (via reaction with a sulfhydryl-reactive reagent comprising iodoacetic acid as described herein below), or the at least one free sulfhydryl of a cysteine residue can be alkylated via reaction with a sulfhydryl-reactive reagent comprising NEM. The stabilizing protein can be BSA, HSA, BGG, and/or Carnation® Instant Nonfat Dry Milk BSA is a preferred stabilizing protein.

IL-18 immunoassays generally can be conducted using any format known in the art, such as, but not limited to, a sandwich format, as further described in U.S. Provisional Patent Application No. 60/981,473 (the '473 application), which was filed on Oct. 19, 2007, and which is hereby incorporated by reference. Specifically, in one format at least two antibodies are employed to separate and quantify IL-18, such as human IL-18, or a fragment thereof in a sample. More specifically, the at least two antibodies bind to certain epitopes of IL-18 (or fragment thereof) forming an immune complex, which is referred to as a "sandwich." Generally, in the immunoassays one or more antibodies can be used to capture the IL-18 (or fragment thereof) in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody," the "detection antibodies," the "conjugate," or the "conjugates").

Excellent immunoassays, particularly, sandwich assays, can be performed using the antibodies directed against the IL-18 as the capture antibodies, detection antibodies, or as capture and detection antibodies. These are described in detail in the '473 application.

Generally speaking, a sample being tested for (for example, suspected of containing) IL-18 (or fragment thereof) can be contacted with at least one capture antibody (or antibodies) and at least one detection antibody (which can be a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a sample suspected of containing IL-18 (or fragment thereof) is first brought into contact with an at least one first capture antibody under conditions that allow the formation of a first antibody/IL-18 complex. If more than one capture antibody is used, a first multiple capture antibody/IL-18 complex is formed. In a sandwich assay, the antibodies, preferably, the at least one capture antibody, are used in molar excess amounts of the maximum amount of IL-18 (or fragment thereof) expected in the test sample. For example, from about 5 µg to about 1 mg of antibody per mL of buffer (e.g., microparticle coating buffer) can be used.

Optionally, prior to contacting the test sample with the at least one capture antibody (for example, the first capture antibody), the at least one capture antibody can be bound to a solid support, which facilitates the separation of the first antibody/IL-18 complex from the test sample. Any solid support known in the art can be used, including, but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind IL-18 (or fragment thereof). Alternatively, the antibody (or antibodies) can be bound with microparticles that have been previously coated with streptavidin or biotin (for example, using Power-Bind™-SA-MP streptavidin-coated microparticles, available from Seradyn, Indianapolis, Ind.). Alternatively, the antibody (or antibodies) can be bound using microparticles that have been previously coated with anti-species-specific monoclonal antibodies. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl) carbodiimide.

After the test sample being tested for and/or suspected of containing IL-18 (or fragment thereof) is brought into contact with the at least one capture antibody (for example, the first capture antibody), the mixture is incubated in order to allow for the formation of a first antibody (or multiple antibody)-IL-18 complex. The incubation can be carried out at a pH of from about 4.5 to about 10.0, at a temperature of from about 2° C. to about 45° C., and for a period from at least about one (1) minute to about eighteen (18) hours, preferably from about 1 to about 20 minutes, most preferably for about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/IL-18 complex, the complex is then contacted with at least one detection antibody (under conditions which allow for the formation of a (first or multiple) capture antibody/IL-18/second antibody detection complex). The at least one detection antibody can be the second, third, fourth, etc. antibodies used in the immunoassay. If the capture antibody/IL-18 complex is contacted with more than one detection antibody, then a (first or multiple) capture antibody/IL-18/(multiple) detection antibody complex is formed. As with the capture antibody (e.g., the first capture antibody), when the at least second (and subsequent) detection antibody is brought into contact with the capture antibody/IL-18 complex, a period of incubation under conditions similar to those described above is required for the formation of the (first or multiple) capture antibody/IL-18/(second or multiple) detection antibody complex. Preferably, at least one detection antibody contains a detectable label. The detectable label can be bound to the at least one detection antibody (e.g., the second detection antibody) prior to, simultaneously with or after the formation of the (first or multiple) capture antibody/IL-18/(second or multiple) detection antibody complex. Any detectable label known in the art can be used. For example, the detectable label can be a radioactive label, such as $^3H$, $^{125}I$, $^{35}S$, $^{14}C$, $^{32}P$, and $^{33}P$, an enzymatic label, such as horseradish peroxidase, alkaline phosphatase, glucose 6-phosphate dehydrogenase, etc., a chemiluminescent label, such as acridinium esters, luminol, isoluminol, thioesters, sulfonamides, phenanthridinium esters, etc., a fluorescence label, such as fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl) carbodiimide, hydrochloride), which is commercially available from Sigma-Aldrich (St. Louis, Mo.). Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester or SPSP-Acridinium Ester.

The (first or multiple) capture antibody/IL-18/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support, it can be simultaneously contacted with the IL-18-containing sample and the at least one second detection antibody to form a first (multiple) antibody/IL-18/second (multiple) antibody complex, followed by removal of the fluid (test sample) from contact with the solid support. If the at least one first capture antibody is not bound to a solid support, then the (first or multiple) capture antibody/IL-18/(second or multiple) detection antibody complex does not have to be removed from the test sample for quantification of the amount of the label.

After formation of the labeled capture antibody/IL-18/detection antibody complex (e.g., the first capture antibody/IL-18/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of IL-18 or IL-18 fragment in the test sample is determined by use of a standard curve that has been generated using serial dilutions of IL-18 or IL-18 fragment of known concentration. Other than using serial dilutions of IL-18 or IL-18 fragment, the standard curve can be generated gravimetrically, by mass spectroscopy and by other techniques known in the art.

The method for assaying a test sample for IL-18 described herein can be used in the diagnosis, prognosis, and assessment of treatment of various conditions and disease states, including, but not limited to, acute renal failure and chronic renal disease. Once the concentration of IL-18 in the test sample (e.g., patient urine sample) has been determined, it can be compared to a predetermined level (e.g., 100 pg/ml, such as for acute renal failure and chronic renal disease) to diagnose whether or not the patient has a certain condition or disease, to prognosticate whether or not the patient is likely to recover from the condition or disease, and to assess the effectiveness of treatment of the patient for a given condition or disease. For example, if the concentration of IL-18 in the sample is less than or equal to a predetermined level, then the patient can be considered to be free from a given condition or disease, to have a favorable prognosis for recovery from a given condition or disease, or to be treated effectively for the condition or disease. In this regard, if the concentration of IL-18 in the sample is above a predetermined level but less than the level in a previous sample from the same patient, the patient can be considered to have a favorable prognosis for recovery or to be treated effectively. If the concentration in the sample is greater than a predetermined level, then the patient can be considered to have a given condition or disease. Whether or not that level is also indicative of a favorable prognosis or effective treatment depends on whether the level in the sample is the same as or lower than that of a previous sample from the same patient. If efficacy of treatment is being monitored, the dosage of the pharmaceutical composition or the type of pharmaceutical composition can be changed in order to realize more effective treatment.

Method of Alkylation

A method of alkylating an isolated or purified IL-18 is also provided. The method comprises contacting the IL-18 with an alkylating agent under conditions that promote alkylation of the free sulfhydryls of the cysteine residues of the IL-18.

Any IL-18, which contains at least one cysteine residue that can form a disulfide bond, or otherwise aggregate, with another cysteine residue in the same molecule or another molecule of IL-18 can be modified, such as by alkylation, e.g., by alkylation in accordance with the methods described herein. Human IL-18 contains four cysteines, namely $Cys^{74}$, $Cys^{104}$, $Cys^{112}$, and $Cys^{163}$, which are highly conserved and of which $Cys^{74}$ and $Cys^{163}$ are required for function (Pei et al., Molec. Immunol. 42: 1367-1373 (2005)). Preferably, the IL-18 is a mature protein, although, in some instances, it can be part of a fusion protein (e.g., a mature protein comprising an additional sequence that renders the mature protein more stable during recombinant production, a secretory sequence, a leader sequence, a pro-sequence, or a sequence that aids in purification). The IL-18 also can be a variant protein, such as one comprising one or more amino acids substitutions (such as up to about 10, up to about 5, up to about 3, or two conservative amino acid substitutions, including the incorporation of one or more unnatural amino acids), deletions, and/or additions (e.g., insertion in an internal region or addition to N- or C-terminus). In this regard, the two most reactive cysteine residues, namely $Cys^{74}$ and $Cys^{104}$, which are presumed to be surface-exposed on folded, mature IL-18, could be independently substituted, e.g., with serine or alanine, and the remaining two cysteines could be alkylated. Desirably, the biological activity of the IL-18 is not adversely affected by the modification, e.g., the alkylation.

The IL-18 can be prepared by any suitable manner as is known in the art. For example, the polypeptide can be isolated from naturally occurring polypeptides, recombinantly produced (e.g., in *E. coli* followed by caspase digestion), synthetically produced, or produced by a combination of two or more of the foregoing methods. See, e.g., Sambrook et al., Molecular Cloning: A Laboratory Manual, $2^{nd}$ ed., Cold Spring Harbor Laboratory Press, Cold Spring Harbor, N.Y. (1989); Kim et al., Biotech. Bioeng. 66: 180-188 (1999); Kim et al., Biotech. Prog. 16: 385-390 (2000); Noren et al., Science 244: 182-188 (1989)); and Swartz et al., U.S. Pat. No. 7,041,479, which issued May 9, 2006). If recombinantly produced in *E. coli*, preferably the codons in the donor cDNA are optimized for expression in *E. coli* (Li et al., Protein Exp. Purif. 32: 110-118 (2003)). Furthermore, IL-18 should be recombinantly produced as its inactive precursor pro-IL-18, which is cleaved by caspase-1, to form the mature active cytokine, and subsequently further purified, such as by ion-exchange chromatography, and preferably frozen until use. Alternatively, the pro-IL-18 nucleotide sequence to be expressed in a host cell can be mutated to comprise another enzyme cleavage site for activation (see, e.g., Liu et al., Cytokine 12(10): 1519-1525 (2000)). Polypeptides can be isolated or purified from recombinant cell cultures by methods known in the art. Such methods include mechanical cell lysis followed by centrifugation, ammonium sulfate or ethanol precipitation, acid extraction, affinity chromatography (e.g., such as capture on immobilized metal affinity chromatography), anion or cation exchange chromatography, phosphocellulose chromatography, high performance liquid chromatography, hydroxylapatite chromatography, and lectin chromatography. Preferably, the isolated or purified IL-18 is free from contaminating proteins (e.g., through dialysis), and contains a single, stable conformer. Conformational homogeneity can be confirmed using ion exchange chromatography, for example. Polypeptides can be refolded in accordance with methods known in the art (e.g., by the addition of a folding enzyme, such as a foldase) to regenerate active conformations after the polypeptides have been denatured during isolation and purification.

Mature, recombinantly produced, human IL-18 (rhIL-18) is commercially available from MBL (Japan). The hIL-18 is recombinantly expressed in *E. coli*. Preferably, the hIL-18 is purified to remove β-mercaptoethanol (BME) and BME-capped hIL-18 prior to alkylation.

Any suitable alkylating agent can be used. Examples of suitable alkylating agents include, but are not limited to, a sulfhydryl-reactive reagent comprising iodoacetic acid, a sulfhydryl-reactive reagent comprising iodoacetamide, a sulfhydryl-reactive reagent comprising NEM, and a sulfhydryl-reactive reagent comprising any one of, N-isopropyliodoacetamide, acrylamide, triethylphosphine with iodoethanol, N-t-butyliodoacetamide, 2-iodo-N-phenylacetamide (iodoacetanilide), N-ethyliodoacetamide, 4-(iodobutyl)triphenylphosphorium, 4-vinylpyridine, N-(2-ferrocene-ethyl)maleimide (Di Gleria et al., FEBS Letter 390(2): 142-144 (1996)), cyclopentenones (Bickley et al., Bioorg. Med. Chem. 12(12): 3221-3227 (2004)), a thioether with iodoacetamide, or N-iodoacetyl-N-(5-sulfo-1-naphthyl)ethylene diamine. Free thiol-reducing agents, such as β-mercaptoethanol (BME), dithiothreitol (DTT), or glutathione, if present in the purified or isolated IL-18, can interfere with alkylation. Therefore, such samples should be dialyzed to remove any such free thiol-reducing agents prior to alkylation with any thiol-alkylating reagent.

When the alkylating agent is a sulfhydryl-reactive reagent comprising iodoacetic acid, preferably the conditions comprise a pH of about 7.2, a reaction time of about two hours, a temperature of about 22° C. (+/−2° C.), and excess sulfhydryl-reactive reagent. For example, from about from a 100- to about a 1.000-fold molar excess of sulfhydryl-reactive reagent over protein, such as from about a 100- to about a 500-fold molar excess or from about a 100- to about a 250-fold molar excess, can be used. Desirably, a capping ratio of about 1 to about 4 is achieved with a sulfhydryl-reactive reagent comprising iodoacetic acid.

When the alkylating agent is a sulfhydryl-reactive reagent comprising iodoacetamide, preferably the conditions comprise a pH of about 7.2, a reaction time of about two hours, a temperature of about 22° C. (+/−2° C.), the absence of light, and excess sulfhydryl-reactive reagent. For example, from about from a 100- to about a 1.000-fold molar excess of sulfhydryl-reactive reagent over protein, such as from about a 100- to about a 500-fold molar excess or from about a 100- to about a 250-fold molar excess, can be used. Desirably, a capping ratio of about 2.5 to about 4 is achieved with a sulfhydryl-reactive reagent comprising iodoacetamide.

The above method of modifying (e.g., by alkylation or acetylation) free sulfhydryls in IL-18 to prevent the formation of disulfide bonds or aggregation can be used to prevent disulfide bond formation or aggregation with respect to other sulfhydryl-containing (i.e., cysteine-containing) proteins. Examples of such proteins include, but are not limited to, soluble FMS-like tyrosine kinase-1 (sFlt-1), placental growth factor (PlGF), neutrophil gelatinase-associated lipocalin (NGAL), β-interferon (β-IFN), Z19 zein, *Mycobacterium tuberculosis* Ftsz, human surfactant protein A locus (SP-A), human immunodeficiency virus (HIV) glycoprotein 41 (gp41), protein kinase C (PKC), and Hepatitis C virus (HCV).

Alkylated IL-18 Pharmaceutical Composition

A pharmaceutical composition comprising a therapeutically or prophylactically effective amount of an alkylated IL-18 is also provided. The composition further comprises a suitable, i.e., pharmaceutically acceptable, carrier, diluent, and/or excipient. Suitable carriers, diluents, and/or excipients are well-known in the art. If desired, another active agent and/or an adjuvant can be included in the pharmaceutical composition.

For administration to an animal, the pharmaceutical composition can be formulated for administration by a variety of routes. For example, the composition can be formulated for oral, topical, rectal or parenteral administration or for administration by inhalation or spray. The term "parenteral" as used herein includes subcutaneous, intravenous, intramuscular, intrathecal, and intrasternal injection and infusion techniques. Various diagnostic compositions and pharmaceutical compositions suitable for different routes of administration and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philadelphia, Pa. (2000). The pharmaceutical composition can be used in the treatment of various conditions in animals, including humans.

The pharmaceutical composition preferably comprises a therapeutically or prophylactically effective amount of alkylated IL-18. The term "therapeutically or prophylactically effective amount" as used herein refers to an amount of alkylated IL-18 needed to treat, ameliorate, inhibit the onset, delay or slow the progression, or prevent a targeted disease or condition, or to exhibit a detectable therapeutic or preventative effect. For alkylated IL-18, the therapeutically or prophylactically effective amount can be estimated initially, for example, either in cell culture assays or in animal models, usually in rodents, rabbits, dogs, pigs or primates. The animal model also can be used to determine the appropriate concentration range and route of administration. Such information then can be used to determine useful doses and routes for administration in the animal to be treated, including humans.

Examples of other active agents, which can be included in the pharmaceutical composition, include, but are not limited to, IL-3, IL-2, IL-12, interferon-α, β or γ, tumor necrosis factor (TNF)-α or β, granulocyte-colony stimulating factor (G-CSF), granulocyte-macrophage colony stimulating factor (GM-CSF), carboquone, cyclophosphamide, aclarubicin, thiotepa, busulfan, anbitabine, cytarabine, 5-fluorouracil, 5-fluoro-1-(tetrahydro-2-furyl)uracil, methotrexate, actinomycin D, chromomycin A3, daunorubicin, doxorubicin, bleomycin, mitomycin C, vincristine, vinblastine, L-asparaginase, radio gold colloidal, Krestin®, picibanil, lentinan, and Maruyama vaccine.

Examples of adjuvants, which can be included in the pharmaceutical composition, include, but are not limited to, those that are known in the art to increase the efficacy or potency of other drugs when given at the same time.

The pharmaceutical composition comprising an alkylated IL-18 can be provided as a therapeutic kit or pack. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit can optionally further contain one or more other active agents for use in combination with the pharmaceutical composition comprising an alkylated IL-18. The kit can optionally contain instructions or directions outlining the method of use or dosing regimen for the pharmaceutical composition comprising an alkylated IL-18 and/or additional active agents or adjuvants.

When one or more components of the kit are provided as solutions, for example an aqueous solution, or a sterile aqueous solution, the container means can itself be an inhalant, syringe, pipette, eye dropper, or other such like apparatus, from which the solution can be administered to a subject or applied to and mixed with the other components of the kit.

The components of the kit also can be provided in dried or lyophilized form, and the kit can additionally contain a suitable solvent for reconstitution of the lyophilized components. Irrespective of the number or types of containers, the kit also can comprise an instrument for assisting with the administration of the composition to a patient. Such an instrument can be an inhalant, a syringe, a pipette, a forceps, a measuring spoon, an eye dropper, or a similar, medically approved, delivery vehicle. Accordingly, the pharmaceutical composition optionally can be part of a kit comprising one or more containers in which the alkylated IL-18, another active agent, and/or the adjuvant can be present in the same or different containers.

Method of Prophylactic or Therapeutic Treatment

A method of treating a patient in therapeutic or prophylactic need of IL-18 is also provided. The method comprises administering to the patient a pharmaceutical composition comprising (i) a therapeutically or prophylactically effective amount of an alkylated IL-18, (ii) a pharmaceutically acceptable carrier, diluent, and/or excipient, and (iii) optionally, another active agent and/or an adjuvant, whereupon the patient is treated.

The method can prove useful in the treatment of infection or risk of infection with *Mycobacteria* (e.g., *M. tuberculosis, M. avium*, and *M. leprae*), *Salmonella typhimurium, Yersinia, Enterocolitica, Chlamydiae trachomatis, Listeria, Leishmania major, Trypanosome cruzi, Cryptococcus neoforms, Streptococcus pneumonia, Plasmodium* such as *Plasmodium berghei, Aspergillus* fumigates, and *Shigella flexneri*. The method also can prove useful in the therapeutic or prophylactic treatment of bladder cancer, septic arthritis, and lipopolysaccharide (LPS)-induced endotoxic shock, as well as in the treatment of infection or risk of infection with viruses, such as Herpes simplex virus (HSV), Vaccinia, human papilloma virus (HPV), human immunodeficiency virus (HIV), feline leukemia virus (FLV), Epstein-Barr virus, Ectromelia, Rubella, Influenza A, encephalomyocarditis virus, and hepatitis virus, and in the treatment of conditions such as condyloma, auto-immune deficiency syndrome (AIDS), candidiasis, malaria, tuberculosis, renal carcinoma, mycosis fungoides, chronic granulomatous diseases, adult-T cell leukemia, chronic myelogenous leukemia, malignant lymphoma, allergies, rheumatism, collagen disease, osteoporosis (in combination with IL-3, can treat or remit leucopenia and thrombocytopenia caused by radiation therapy or chemotherapy, leukemia, myeloma), and wound healing. In this regard, alkylated IL-18 can be included in a composition that induces an immune response against *Schistosoma mansoni*, e.g., a vaccine composition.

EXAMPLES

The following examples serve to illustrate the present disclosure. The examples are not intended to limit the scope of the claimed invention in any way.

Example 1

This example describes a method of alkylating sulfhydryl groups of cysteine residues in IL-18 with iodoacetamide.

rhIL-18 was obtained from MBL (Japan). A stock solution (150 mM) of iodoacetamide in high pressure liquid chromatography (HPLC) grade water was prepared in a light-sensitive container (or a container covered with aluminum foil to prevent exposure to light) and immediately added to the rhIL-18. A 4.0 µL volume of iodoacetamide stock solution was added to 36 µL of IL-18 (0.577 mg/mL parent concentration) in phosphate-buffered saline (PBS) (20.8 µg of IL-18 in a reaction mixture containing 15 mM iodoacetamide) in a light-sensitive container (or aluminum foil-covered container), and the resulting mixture was vortexed. The reaction mixture was incubated at room temperature (RT) for 2 hours in the dark. Excess and/or unreacted iodoacetamide was removed from the alkylated IL-18 by buffer exchange with PBS using Pierce Zebra desalting spin columns (Pierce Biotechnology, Rockford, Ill.). The alkylated IL-18 was stored long-term at about 2° C. to about 8° C. or about −20° C.

Example 2

This example describes a method of alkylating sulfhydryl groups on cysteine residues of IL-18 with sodium iodoacetate.

rhIL-18 was obtained from MBL (Japan). A stock solution (150 mM) of sodium iodoacetate in HPLC grade water was prepared in a polypropylene microcentrifuge tube immediately before application to the rhIL-18. A 5.0 µL volume of the sodium iodoacetate stock solution was added to 45 µL of rhIL-18 (0.577 mg/mL parent concentration) in PBS (26 µg of IL-18 in a reaction mixture containing 15 mM sodium iodoacetate). The reaction mixture was incubated at RT for 2 hours in the dark. Excess and/or unreacted sodium iodoacetate was removed from the alkylated IL-18 by buffer exchange with PBS using Pierce Zebra desalting spin columns (Pierce Biotechnology). The alkylated IL-18 was stored long-term at about 2° C. to about 8° C. or about −20° C.

Example 3

This example describes electrospray ionization-mass spectrometry (ESI-MS) analysis of rhIL-18 alkylated in accordance with the methods of Examples 1 and 2 as compared to unmodified rhIL-18.

Samples of unmodified rhIL-18 and alkylated rhIL-18 were equilibrated to RT. TCEP-HCl (Tris(2-carboxyethyl) phosphine hydrochloride; Pierce Protein Research Products, Thermo Fisher Scientific Inc.) was added to the rhIL-18 prior to alkylation to eliminate BME in order to calculate capping ratios more accurately. Samples were cleaned using Microcon YM-10 centrifugal filter units (Millipore, Billerica, Mass.). A 25 mM ammonium bicarbonate solution was prepared by dissolving 0.079 g of ammonium bicarbonate in 40 mL of water. Five hundred µL of 25 mM ammonium bicarbonate solution were added to Microcon YM-10 centrifugal filter units, and centrifuged at 14,000 rpm for 15 minutes at 8° C. The remaining buffer was discarded. 20 µL of unmodified rhIL-18 (in duplicate), 20 µL of unmodified and TCEP-reduced rhIL-18, 20 µL of alkylated rhIL-18, and 20 µL of alkylated and TCEP-reduced rhIL-18 were separately added with 480 µL of 25 mM ammonium bicarbonate solution to the Microcon YM-10 centrifugal filter units, and the units were vortexed and then centrifuged at 14,000 rpm at 8° C. for 45 minutes. Then 500 µL of HPLC water were added to each unit, and the unit was vortexed and then centrifuged at 14,000 rpm at 8° C. for 40 minutes. Afterwards, 200 µL of HPLC water were added to each unit, and the unit was vortexed and then centrifuged at 14,000 rpm at 8° C. for 23 minutes.

Twenty μL of each of the desalted samples were added to separate autosampler vial inserts. Four μL of each sample were injected for liquid chromatography/mass spectrometry (LC/MS) according to the Q-Star LCMS method (Applied Biosystems, Foster City, Calif.). The most abundant peak (at 18,388+/−1 Da) for the rhIL-18 alkylated with iodoacetamide had three cysteines modified with carbamidomethyl groups; another peak (at 18,446 Da) had four cysteines modified with carbamidomethyl groups. The most abundant peak (at 18,334 Da) for the rhIL-18 alkylated with sodium iodoacetate had two cysteines modified with carboxymethyl groups; another peak (at 18,391 Da) had three cysteines modified with carboxymethyl groups.

Example 4

This example describes the preparation of a series of calibrating compositions comprising alkylated IL-18.

A series of alkylated IL-18 calibrating compositions was prepared at concentrations of 0, 25, 75, 250, 600, and 1,000 pg/mL. The compositions were prepared in 35 mM phosphate, 150 mM NaCl, 1% BSA, and 0.1% $NaN_3$, at pH 5.8-6.0.

Example 5

This example compares the stability of rhIL-18 calibrating compositions comprising various concentrations of bovine serum albumin (BSA), alone or in further combination with Proclin 300, or azide and Proclin 300.

A chemiluminescent microparticle immunoassay employing the ARCHITECT® automated analyzer (Abbott Laboratories, Abbott Park, Ill.; see also U.S. Pat. Nos. 5,795,784 and 5,856,194, both of which are incorporated herein by reference in their entireties) was used in the comparison. A sample of a calibrating composition was mixed with a microparticle reagent, which contained paramagnetic, streptavidin-coated microparticles coated (50 μg/mL) with biotin-labeled anti-IL-18 antibody or paramagnetic microparticles coated with anti-IL-18 antibody (75 μg/mL) chemically attached to the microparticles with EDAC (1-ethyl-3-(3-dimethylaminopropyl) carbodiimide, hydrochloride) and reacted for 18 minutes at 37° C. on the ARCHITECT® analyzer. After the 18-minute reaction, the microparticles were washed to eliminate any unbound sample, CPSP-conjugated or SPSP-conjugated anti-IL-18 antibody (300 ng/mL) was added, and the sample was incubated for four minutes on the ARCHITECT® analyzer. The CPSP/SPSP-conjugated anti-IL-18 antibody bound to the IL-18 already bound to the anti-IL-18 antibody coated on the microparticles. After four minutes, the unbound conjugate was eliminated by washing, and pre-trigger and trigger solutions were added to cause a chemiluminescent reaction, which was measured in RLUs.

At day 0, the data were as set forth in Tables 1 and 2 below.

TABLE 1

| [IL-18] | Calibrator Signal (RLU) | | | |
|---|---|---|---|---|
| pg/mL | A | B | C | D |
| 0 | 339.33 | 363.67 | 355.50 | |
| 25 | 5,160.00 | 5,014.33 | 5,749.33 | 5,132.00 |
| 75 | 16,571.33 | 14,861.33 | 15,436.67 | 15,630.00 |
| 250 | 50,419.33 | 46,732.00 | 50,661.67 | 47,609.33 |
| 600 | 118,008.33 | 113,247.00 | 112,790.67 | 113,967.33 |
| 1,000 | 215,213.67 | 190,713.67 | 190,681.33 | 188,152.67 |
| RLU (1,000-0) | 214,874.33 | 190,350.00 | 190,325.83 | 188,152.67 |

In Table 1, calibrator A=IL-18 and 0.01% BSA, calibrator B=IL-18, 5% BSA, and 0.1% Proclin 300 (Sigma-Aldrich Co.), calibrator C=IL-18 and 10.01% BSA, and calibrator D=IL-18, 5.01% BSA, 0.14% Proclin 300, and 0.1% azide.

TABLE 2

| [IL-18] | Calibrator Signal (RLU) | | | |
|---|---|---|---|---|
| pg/mL | E | F | G | H |
| 0 | 468.67 | 319.67 | 408.33 | 320.50 |
| 25 | 5,383.00 | 5,392.33 | 5,077.00 | 4,792.33 |
| 75 | 14,946.00 | 14,965.67 | 14,142.00 | 13,557.00 |
| 250 | | | | |
| 600 | 116,496.33 | 115,243.00 | 118,361.00 | 102,023.67 |
| 1,000 | 183,775.67 | 182,217.33 | 200,112.67 | 171,345.67 |
| RLU (1,000-0) | 183,307.00 | 181,897.67 | 199,704.33 | 171,025.17 |

In Table 2, calibrator E=IL-18 and 2.51% BSA, calibrator F=IL-18 and 5.01% BSA, calibrator G=IL-18 and 0.11% BSA, and calibrator H=IL-18 and 1.01% BSA.

At day 6 at about 37° C., the data were as follows in Tables 3 and 4.

TABLE 3

| [IL-18] | Calibrator Signal (RLU) | | | |
|---|---|---|---|---|
| pg/mL | A | B | C | D |
| 0 | 416.50 | 359.00 | | |
| 25 | 1,955.00 | 2,826.67 | 5,076.67 | 3,932.33 |
| 75 | 4,465.33 | 7,426.00 | 14,417.33 | 10,930.33 |
| 250 | 9,826.00 | 23,419.00 | 45,900.67 | 34,864.00 |
| 600 | 13,677.67 | 54,232.33 | 108,667.00 | 84,146.00 |
| 1,000 | 17,009.33 | 88,473.67 | 171,978.00 | 133,020.67 |
| RLU (1,000-0) | 16,592.83 | 88,114.67 | 171,978.00 | 133,020.67 |

TABLE 4

| [IL-18] | Calibrator Signal (RLU) | | | |
|---|---|---|---|---|
| pg/mL | E | F | G | H |
| 0 | | | | |
| 25 | 4,670.33 | 4,887.00 | 2,708.00 | 3,929.67 |
| 75 | | 13,939.33 | 7,255.33 | 10,944.33 |
| 250 | 13,262.00 | | | |
| 600 | 101,118.33 | 105,298.33 | 31,951.67 | 79,874.67 |
| 1,000 | 157,013.00 | 167,832.33 | 44,028.00 | 118,887.00 |
| RLU (1,000-0) | 157,013.00 | 167,832.33 | 44,028.00 | 118,887.00 |

The mean RLU differential between day 0 and day 6 at about 37° C. was −79.24 for calibrator A, −49.85 for calibrator B, −8.23 for calibrator C, −27.14 for calibrator D, −13.67 for calibrator E, −8.19 for calibrator F, −61.59 for calibrator G, and −22.40 for calibrator H. Thus, the addition of BSA in increasing amounts from about 0.01% to about 5.0% reduced the loss of activity of unalkylated IL-18 from about 79% to about 8%. The stabilizing effect of about 5.0% BSA was largely negated by the addition of about 0.1% Proclin 300 (49.85% loss in activity) alone or in further combination with about 0.1% azide (27.14% loss in activity).

At day 6 at about 2° C. to about 8° C., the data were as follows in Tables 5 and 6:

TABLE 5

| [IL-18] pg/mL | Calibrator Signal (RLU) | | | |
|---|---|---|---|---|
| | A | B | C | D |
| 0 | 507.33 | 534.67 | 543.33 | |
| 25 | 5,164.00 | 5,593.67 | 5,872.00 | 5,395.67 |
| 75 | 15,371.33 | 15,293.67 | 16,155.67 | 15,500.00 |
| 250 | 51,273.67 | 47,171.33 | 51,886.33 | 49,976.00 |
| 600 | 117,531.33 | 113,315.00 | 120,953.00 | 118,027.67 |
| 1,000 | 206,571.00 | 189,772.33 | 196,439.00 | 187,500.67 |
| RLU (1,000-0) | 206,063.67 | 189,237.67 | 195,895.67 | 187,500.67 |

TABLE 6

| [IL-18] pg/mL | Calibrator Signal (RLU) | | | |
|---|---|---|---|---|
| | E | F | G | H |
| 0 | 509.00 | 436.00 | 579.00 | 555.67 |
| 25 | 5,648.33 | 5,842.00 | 4,740.00 | 4,942.50 |
| 75 | 15,606.33 | 16,562.00 | 12,798.33 | 14,553.00 |
| 250 | | | | |
| 600 | 117,643.67 | 119,190.33 | 114,213.00 | 105,616.67 |
| 1,000 | 189,842.33 | 192,634.00 | 202,040.50 | 180,334.00 |
| RLU (1,000-0) | 189,333.33 | 192,198.00 | 201,461.50 | 179,778.33 |

The mean RLU differential between day 0 and day 6 at about 2° C. to about 8° C. was −1.98 for calibrator A, 2.99 for calibrator B, 3.89 for calibrator C, 2.50 for calibrator D, 3.41 for calibrator E, 7.04 for calibrator F, −4.67 for calibrator G, and 4.81 for calibrator H. Thus, unalkylated IL-18 in the presence of various concentrations of BSA, alone or in further combination with either Proclin 300 or Proclin 300 and azide, remained relatively stable at about 2° C. to about 8° C. after 6 days.

Example 6

This example compares the stability of rhIL-18 calibrating compositions comprising various concentrations of various proteins and azide.

The chemiluminescent microparticle immunoassay described in Example 6 was used in the comparison.

At day 0, the data were as follows in Table 7:

TABLE 7

| [IL-18] pg/mL | Calibrator Signal (RLU) | | | | | | |
|---|---|---|---|---|---|---|---|
| | A | B | C | D | E | F | G |
| 0 | 703.67 | 534.67 | 2,964.67 | 618.67 | 1,050.00 | 538.00 | 850.00 |
| 25 | 3,833.33 | 3,641.67 | 6,297.00 | 3,943.67 | 4,170.00 | 4,160.33 | 3,786.33 |
| 75 | 10,196.33 | 9,654.00 | 13,526.33 | 11,351.00 | 10,030.67 | 11,563.67 | 10,949.00 |
| 250 | 36,219.33 | 31,176.67 | 37,244.00 | 34,991.00 | 30,644.67 | 35,027.00 | 35,183.33 |
| 600 | 87,743.00 | 72,902.00 | 85,076.33 | 86,521.67 | 68,710.33 | 82,514.67 | 92,153.33 |
| 1,000 | 148,531.67 | 118,162.00 | 136,518.33 | 145,330.33 | 115,469.67 | 132,058.33 | 147,957.00 |
| RLU (1,000-0) | 147,828.00 | 117,627.33 | 133,553.67 | 144,711.67 | 114,419.67 | 131,520.33 | 147,107.00 | wherein calibrator A=IL-18, calibrator B=IL-18 and 1% BSA, calibrator C=IL-18 and 1% human serum albumin (HSA), calibrator D=IL-18 and 1% fish gel, calibrator E=IL-18 and 1% bovine γ-globulin (BGG), calibrator F=IL-18 and 1% Carnation® Instant Nonfat Dry Milk (Nestle U.S.A.), and G=IL-18 and 1% casein.

At day 6 at about 37° C., the data were as follows in Table 8:

TABLE 8

| [IL-18] pg/mL | Calibrator Signal (RLU) | | | | | | |
|---|---|---|---|---|---|---|---|
| | A | B | C | D | E | F | G |
| 0 | 590.00 | 610.00 | 1,975.67 | 590.33 | 859.33 | 457.33 | 595.33 |
| 25 | 1,098.00 | 3,022.67 | 4,343.67 | 1,174.00 | 3,347.00 | 3,173.67 | 1,140.00 |
| 75 | 1,781.67 | 8,401.33 | 9,456.33 | 2,672.33 | 8,508.00 | 8,114.00 | 2,250.67 |
| 250 | 3,875.33 | 24,667.33 | 27,479.00 | 7,090.67 | 25,021.00 | 25,210.00 | 6,305.67 |
| 600 | 6,052.33 | 55,100.33 | 58,642.00 | 11,822.67 | 59,034.00 | 60,117.33 | 11,499.33 |
| 1,000 | 7,647.33 | 87,489.67 | 96,390.00 | 15,954.67 | 93,280.00 | 93,402.33 | 14,913.67 |
| RLU (1,000-0) | 7,057.33 | 86,879.67 | 94,414.33 | 15,364.33 | 92,420.67 | 92,945.00 | 14,318.33 |

The mean RLU differential between day 0 and day 6 at about 37° C. was −86.23 for calibrator A, −20.25 for calibrator B, −29.56 for calibrator C, −80.36 for calibrator D, −17.31 for calibrator E, −27.60 for calibrator F, and −81.77 for calibrator G. Thus, in the absence of BSA, IL-18 lost over 86% of its activity over six days at about 37° C. The addition of BSA (1%) reduced this loss in activity to about 20%. HSA (1%), BGG (1%), and Carnation® Instant Nonfat Dry Milk (1%) provided losses in activity ranging from about 30% to about 17% to about 28%, respectively. Achieving a loss in signal of about 20% or less over six days at 37° C. allows compositions comprising IL-18 to be shipped unfrozen and without ice.

At day 6 at about 2° C. to about 8° C., the data were as follows in Table 9:

TABLE 9

| [IL-18] pg/mL | Calibrator Signal (RLU) | | | | | | |
|---|---|---|---|---|---|---|---|
| | A | B | C | D | E | F | G |
| 0 | 664.00 | 644.67 | 3,039.67 | 574.00 | 1,000.67 | 462.00 | 668.67 |
| 25 | 3,236.33 | 3,746.00 | 6,456.33 | 3,654.67 | 4,130.00 | 4,013.33 | 3,371.00 |
| 75 | 8,878.00 | 10,183.67 | 13,353.00 | 10,251.00 | 10,212.67 | 10,401.33 | 9,815.00 |
| 250 | 32,066.00 | 30,380.33 | 37,410.67 | 31,600.67 | 31,138.00 | 34,201.67 | 34,801.33 |
| 600 | 77,498.33 | 70,317.00 | 84,419.67 | 78,106.67 | 70,731.67 | 82,085.67 | 84,515.67 |
| 1,000 | 124,204.33 | 107,981.67 | 135,082.00 | 130,722.00 | 115,938.00 | 131,527.00 | 134,778.33 |
| RLU (1,000-0) | 123,540.33 | 107,337.00 | 132,042.33 | 130,148.00 | 114,937.33 | 131,065.00 | 134,109.67 |

The mean RLU differential between day 0 and day 6 at about 2° C. to about 8° C. was −13.60 for calibrator A, −1.27 for calibrator B, −0.03 for calibrator C, −9.30 for calibrator D, 1.16 for calibrator E, −3.37 for calibrator F, and −7.92 for calibrator G. Thus, in the absence of BSA, IL-18 lost over 13% of its activity over six days at about 2° C. to about 8° C. The addition of BSA (1%) reduced this loss in activity to about 1%. HSA (1%) and Carnation® Instant Nonfat Dry Milk (1%) provided losses in activity ranging from less than 1% to less than 4%, respectively. After six days, analysis of proteins, like casein and fish gelatin, which exhibited the same loss in signal as the unalkylated IL-18 without BSA, was discontinued, since no improvement in antigen stability was observed.

At day 14 at about 37° C., the data were as follows in Table 10:

TABLE 10

| [IL-18] pg/mL | Calibrator Signal (RLU) | | | | | | |
|---|---|---|---|---|---|---|---|
| | A | B | C | D | E | F | G |
| 0 | 585.00 | 512.00 | 1,486.50 | — | 751.00 | 685.67 | — |
| 25 | 691.00 | 2,955.33 | 3,657.00 | — | 2,897.33 | 2,888.33 | — |
| 75 | 981.67 | 7,751.33 | 8,173.33 | — | 7,116.33 | 7,327.00 | — |
| 250 | 1,515.00 | 22,081.33 | 23,283.00 | — | 22,299.00 | 20,573.00 | — |
| 600 | 2,063.33 | 47,509.00 | 53,847.00 | — | 50,597.00 | 48,878.00 | — |
| 1,000 | 3,292.00 | 77,048.67 | 79,434.00 | — | 77,905.00 | 76,883.67 | — |
| RLU (1,000-0) | 2,707.00 | 76,896.67 | 77,947.50 | — | 77,154.00 | 76,198.00 | — |

The mean RLU differential between day 0 and day 14 at about 37° C. was −92.72 for calibrator A, −27.41 for calibrator B, −39.50 for calibrator C, −29.14 for calibrator E, and −38.20 for calibrator F. Thus, in the absence of BSA, IL-18 lost almost 93% of its activity over 14 days at about 37° C. The addition of BSA (1%) reduced this loss in activity to about 27%. HSA (1%), BGG (1%), and Carnation® Instant Nonfat Dry Milk (1%) provided losses in activity ranging from about 39.5% to about 29.14% to about 38.20%, respectively.

At day 14 at about 2° C. to about 8° C., the data were as follows in Table 11:

TABLE 11

| [IL-18] pg/mL | Calibrator Signal (RLU) | | | | | | |
|---|---|---|---|---|---|---|---|
| | A | B | C | D | E | F | G |
| 0 | 560.67 | 558.00 | 3,007.00 | — | 875.00 | 570.67 | — |
| 25 | 2,838.67 | 3,614.67 | 6,380.00 | — | 3,683.00 | 3,760.33 | — |

TABLE 11-continued

| [IL-18] pg/mL | Calibrator Signal (RLU) | | | | | | |
|---|---|---|---|---|---|---|---|
| | A | B | C | D | E | F | G |
| 75 | 8,021.67 | 10,082.00 | 13,469.67 | — | 9,668.00 | 10,411.33 | — |
| 250 | 28,780.67 | 31,370.33 | 36,428.00 | — | 29,455.33 | 33,334.00 | — |
| 600 | 73,268.33 | 69,380.00 | 84,220.33 | — | 66,743.33 | 78,334.33 | — |
| 1,000 | 122,962.00 | 119,554.67 | 137,321.67 | — | 113,919.67 | 128,005.67 | — |
| RLU (1,000-0) | 122,401.33 | 118,996.67 | 134,314.67 | — | 113,044.67 | 127,435.00 | — |

The mean RLU differential between day 0 and day 14 at about 2° C. to about 8° C. was −20.31 for calibrator A, 0.13 for calibrator B, −0.34 for calibrator C, −4.68 for calibrator E, and −6.51 for calibrator F. Thus, in the absence of BSA, IL-18 lost over 20% of its activity over 14 days at about 2° C. to about 8° C. The addition of BSA (1%) almost completely reduced this loss in activity. HSA (1%), BGG (1%), and Carnation® Instant Nonfat Dry Milk (1%) provided losses in activity ranging from about 0.34% to about 4.68% to about 6.51%, respectively.

At day 32 at about 2° C. to about 8° C., the data were as follows in Table 12:

TABLE 12

| [IL-18] pg/mL | Calibrator Signal (RLU) | | | | | | |
|---|---|---|---|---|---|---|---|
| | A | B | C | D | E | F | G |
| 0 | — | 588.00 | 3,092.50 | — | — | — | — |
| 25 | — | 3,698.50 | 6,416.00 | — | 3,897.50 | — | — |
| 75 | — | 10,627.50 | 13,711.50 | — | 10,308.00 | — | — |
| 250 | — | 31,586.00 | 37,285.50 | — | 30,597.00 | — | — |
| 600 | — | 76,046.50 | 86,503.00 | — | — | — | — |
| 1,000 | — | 124,472.50 | 131,727.50 | — | — | — | — |
| RLU (1,000-0) | — | 123,884.50 | 128,635.00 | — | 0.00 | — | — |

The mean RLU differential between day 0 and day 32 at about 2° C. to about 8° C. was 4.52 for calibrator B, 0.31 for calibrator C, and −1.31 for calibrator E. Thus, calibrator compositions comprising 1% BSA, HSA or BGG remained stable over 32 days at about 2° C. to about 8° C.

Example 7

This example compares the stability of calibrating compositions comprising various rhIL-18s in the presence of 1% or 5% BSA at about 2° C. to about 8° C. and 37° C.

The chemiluminescent microparticle immunoassay described in Example 6 was used in the comparison.

At day 0, the data were as follows in Tables 13 and 14:

TABLE 13

| [IL-18] pg/mL | Calibrator Signal (RLU) | | | |
|---|---|---|---|---|
| | A | B | C | D |
| 0 | 362.33 | 362.33 | 409.67 | 584.33 |
| 25 | 4,878.00 | 4,689.67 | 4,917.00 | 7,332.67 |
| 75 | 14,190.67 | 13,776.00 | 15,064.67 | 20,780.00 |
| 250 | 45,246.00 | 46,504.00 | 46,239.67 | 66,669.67 |
| 600 | 109,898.67 | 107,473.00 | 109,682.00 | 161,935.67 |
| 1,000 | 183,265.00 | 176,521.33 | 187,562.00 | 250,861.33 |
| RLU (1,000-0) | 182,902.67 | 176,159.00 | 187,152.33 | 250,277.00 | wherein calibrator A=IL-18 and 1% BSA, calibrator B=alkylated IL-18 and 1% BSA, calibrator C=IL-18, 1% BSA, and 2% sorbitol, and D=IL-18, 1% BSA, and 1.5 mM 2-diethylaminoethanethiol (DEAE). DEAE is a reducing agent. The calibrator diluent contained 35 mM phosphate, 150 mM NaCl, and 0.1% azide, pH 5.8.

TABLE 14

| [IL-18] pg/mL | Calibrator Signal (RLU) | | | | |
|---|---|---|---|---|---|
| | E | F | G | H | I |
| 0 | 488.67 | 488.67 | 488.67 | 488.67 | 488.67 |
| 25 | 5,191.33 | 4,539.00 | 8,300.67 | 9,027.00 | 8,357.33 |
| 75 | 13,786.00 | 11,102.00 | 22,948.67 | 25,289.33 | 24,937.33 |
| 250 | 47,510.00 | 37,394.00 | 74,871.33 | 80,962.67 | 78,745.67 |
| 600 | 109,502.33 | 85,993.33 | 172,168.67 | 184,339.67 | 182,586.67 |
| 1,000 | 170,181.00 | 142,616.00 | 272,065.67 | 301,608.67 | 298,341.67 |
| RLU (1,000-0) | 169,692.33 | 142,127.33 | 271,577.00 | 301,120.00 | 297,853.00 | wherein calibrators E-I comprise 5% BSA with different lots of rhIL-18.

At day 6 at 37° C., the data were as follows in Tables 15 and 16:

TABLE 15

| [IL-18] | Calibrator Signal (RLU) | | | |
|---|---|---|---|---|
| pg/mL | A | B | C | D |
| 0 | 426.00 | 426.00 | 310.33 | 402.00 |
| 25 | 3,636.67 | 4,814.00 | 3,635.67 | 7,034.33 |
| 75 | 10,372.33 | 13,061.00 | 10,771.00 | 19,064.33 |
| 250 | 34,749.33 | 43,923.00 | 32,751.00 | 62,631.33 |
| 600 | 73,599.33 | 100,454.67 | 73,273.00 | 146,932.33 |
| 1,000 | 113,174.33 | 163,080.00 | 117,144.33 | 224,747.33 |
| RLU (1,000-0) | 112,748.33 | 162,654.00 | 116,834.00 | 224,345.33 |

TABLE 16

| [IL-18] | Calibrator Signal (RLU) | | | | |
|---|---|---|---|---|---|
| pg/mL | E | F | G | H | I |
| 0 | 497.67 | 497.67 | 497.67 | 497.67 | 497.67 |
| 25 | 4,351.67 | 1,247.67 | 6,415.00 | 7,371.33 | 7,105.33 |
| 75 | 11,269.67 | 2,714.33 | 18,824.33 | 20,699.00 | 21,264.57 |
| 250 | 37,079.67 | 8,346.33 | 62,299.67 | 67,800.33 | 67,117.33 |
| 600 | 86,864.00 | 18,625.67 | 143,178.00 | 156,821.67 | 148,313.67 |
| 1,000 | 135,337.33 | 31,392.33 | 224,154.67 | 252,102.00 | 247,581.00 |
| RLU (1,000-0) | 134,839.67 | 30,894.67 | 223,657.00 | 251,604.33 | 247,083.33 |

TABLE 17

| [IL-18] | Calibrator Signal (RLU) | | | |
|---|---|---|---|---|
| pg/mL | A | B | C | D |
| 0 | 378.00 | 378.00 | 337.00 | 430.67 |
| 25 | 4,838.67 | 4,933.00 | 4,767.33 | 7,493.67 |
| 75 | 14,274.00 | 14,168.67 | 14,258.00 | 21,413.33 |
| 250 | 46,210.00 | 44,431.33 | 45,505.33 | 70,692.00 |
| 600 | 103,788.00 | 106,477.67 | 103,064.33 | 169,394.67 |
| 1,000 | 168,326.00 | 169,697.00 | 164,963.67 | 256,770.67 |
| RLU (1,000-0) | 167,948.00 | 169,319.00 | 164,626.67 | 256,340.00 |

The mean RLU differential between day 0 and day 6 at about 37° C. was −29.37 for calibrator A, −4.45 for calibrator B, −30.89 for calibrator C, −7.61 for calibrator D, −19.51 for calibrator E, −76.41 for calibrator F, −18.39 for calibrator G, −16.82 for calibrator H, and −16.05 for calibrator I. Thus, alkylated IL-18 in the presence of 1% BSA lost less activity over 6 days at 37° C. than unalkylated IL-18 in the presence of 1% or 5% BSA. The addition of DEAE to alkylated IL-18 in the presence of 1% BSA did not appear to improve stability.

At day 6 at about 2° C. to about 8° C., the data were as follows in Tables 17 and 18:

TABLE 18

| [IL-18] | Calibrator Signal (RLU) | | | | |
|---|---|---|---|---|---|
| pg/mL | E | F | G | H | I |
| 0 | 505.50 | 505.50 | 505.50 | 505.50 | 505.50 |
| 25 | 5,511.00 | 4,390.00 | 7,839.00 | 8,483.67 | 8,683.67 |
| 75 | 14,344.33 | 11,015.33 | 22,193.00 | 25,305.33 | 24,938.67 |
| 250 | 48,800.67 | 36,437.00 | 73,073.33 | 79,652.67 | 79,231.00 |
| 600 | 109,519.00 | 83,322.33 | 164,340.00 | 187,719.00 | 181,854.33 |
| 1,000 | 178,662.67 | 141,545.33 | 273,394.67 | 301,130.33 | 293,884.67 |
| RLU (1,000-0) | 178,157.17 | 141,039.83 | 272,889.17 | 300,624.83 | 293,379.17 |

The mean RLU differential between day 0 and day 6 at about 2° C. to about 8° C. was −2.36 for calibrator A, −0.24 for calibrator B, −5.61 for calibrator C, 3.65 for calibrator D, 3.58 for calibrator E, −2.10 for calibrator F, −3.06 for calibrator G, −1.20 for calibrator H, and 0.53 for calibrator I. Thus, unalkylated IL-18 in the presence of 1% or 5% BSA and alkylated IL-18 in the presence of 1% BSA were both relatively stable at about 2° C. to about 8° C. over six days.

At day 14 at about 37° C., the data were as follows in Tables 19 and 20:

TABLE 19

| [IL-18] | Calibrator Signal (RLU) | | | |
|---|---|---|---|---|
| pg/mL | A | B | C | D |
| 0 | 403.00 | 403.00 | 366.00 | 359.33 |
| 25 | 3,230.67 | 4,581.67 | 3,048.00 | 5,316.33 |
| 75 | 9,447.00 | 12,498.00 | 8,905.67 | 15,512.33 |
| 250 | 28,218.33 | 39,926.67 | 27,630.33 | 50,250.33 |
| 600 | 61,570.67 | 94,138.67 | 61,532.00 | 111,746.67 |
| 1,000 | 97,435.00 | 151,045.33 | 94,363.33 | 170,292.00 |
| RLU (1,000-0) | 97,032.00 | 150,642.33 | 93,997.33 | 169,932.67 |

TABLE 20

| [IL-18] | Calibrator Signal (RLU) | | | | |
|---|---|---|---|---|---|
| pg/mL | E | F | G | H | I |
| 0 | 288.50 | 288.50 | 288.50 | 288.50 | 288.50 |
| 25 | 3,420.00 | 894.00 | 6,033.67 | 7,080.33 | 6,438.33 |
| 75 | 9,646.33 | 1,907.00 | 16,922.00 | 18,426.00 | 18,209.33 |
| 250 | 31,844.67 | 5,874.67 | 54,267.67 | 60,071.33 | 58,646.00 |
| 600 | 69,940.67 | 13,653.00 | 124,903.00 | 140,162.33 | 129,984.67 |
| 1,000 | 118,406.00 | 23,242.00 | 193,077.33 | 218,294.00 | 211,221.33 |
| RLU (1,000-0) | 118,117.50 | 22,953.50 | 192,788.83 | 218,005.50 | 210,932.83 |

The mean RLU differential between day 0 and day 14 at about 37° C. was −39.13 for calibrator A, −10.51 for calibrator B, −42.55 for calibrator C, −28.12 for calibrator D, −32.73 for calibrator E, −83.05 for calibrator F, −27.52 for calibrator G, −25.22 for calibrator H, and −26.70 for calibrator I. Thus, the alkylated IL-18 in the presence of 1% BSA only lost about 10% activity over 14 days at about 37° C., whereas the unalkylated IL-18 in the presence of 1% or 5% BSA lost as much as about 39% activity over 14 days at about 37° C.

At day 14 at about 2° C. to about 8° C., the data were as follows in Tables 21 and 22:

TABLE 21

| [IL-18] | Calibrator Signal (RLU) | | | |
|---|---|---|---|---|
| pg/mL | A | B | C | D |
| 0 | 452.33 | 452.33 | 366.00 | 365.00 |
| 25 | 4,870.67 | 4,522.00 | 4,846.33 | 7,507.00 |

TABLE 21-continued

| [IL-18] | Calibrator Signal (RLU) | | | |
|---|---|---|---|---|
| pg/mL | A | B | C | D |
| 75 | 13,621.00 | 13,652.67 | 13,798.00 | 21,940.67 |
| 250 | 43,768.33 | 45,021.67 | 43,729.67 | 70,523.67 |
| 600 | 100,538.33 | 102,895.67 | 103,322.67 | 168,893.67 |
| 1,000 | 162,603.00 | 172,493.33 | 160,449.33 | 261,274.33 |
| RLU (1,000-0) | 162,150.67 | 172,041.00 | 160,083.33 | 260,909.33 |

TABLE 22

| [IL-18] | Calibrator Signal (RLU) | | | | |
|---|---|---|---|---|---|
| pg/mL | E | F | G | H | I |
| 0 | 473.00 | 473.00 | 473.00 | 473.00 | 473.00 |
| 25 | 5,178.67 | 4,444.00 | 7,518.33 | 8,658.67 | 8,382.33 |
| 75 | 14,460.33 | 10,871.67 | 22,246.67 | 25,320.67 | 24,071.67 |
| 250 | 47,452.00 | 36,209.33 | 70,144.00 | 78,149.33 | 76,217.00 |
| 600 | 105,632.33 | 80,161.00 | 161,490.00 | 182,933.33 | 177,331.67 |
| 1,000 | 176,371.00 | 136,602.00 | 254,648.33 | 287,357.00 | 287,842.67 |
| RLU (1,000-0) | 175,898.00 | 136,129.00 | 254,175.33 | 286,884.00 | 287,369.67 |

The mean RLU differential between day 0 and day 14 at 2° C. to about 8° C. was −5.44 for calibrator A, −2.84 for calibrator B, −7.11 for calibrator C, 4.44 for calibrator D, 0.93 for calibrator E, −3.67 for calibrator F, −6.28 for calibrator G, −2.58 for calibrator H, and −2.56 for calibrator I. Thus, unalkylated IL-18 in the presence of 1% or 5% BSA and alkylated IL-18 in the presence of 1% BSA remained relatively stable at about 2° C. to about 8° C. over 14 days.

At day 31 at about 2° C. to about 8° C., the data were as follows in Tables 23 and 24:

TABLE 23

| [IL-18] | Calibrator Signal (RLU) | | | |
|---|---|---|---|---|
| pg/mL | A | B | C | D |
| 0 | 404.67 | 404.67 | — | 483.33 |
| 25 | 4,655.33 | 4,686.33 | — | 7,418.00 |
| 75 | 13,788.00 | 14,496.67 | — | 22,319.33 |
| 250 | 43,936.00 | 43,287.00 | — | 72,261.67 |
| 600 | 100,660.67 | 100,165.33 | — | 167,494.00 |
| 1,000 | 160,150.33 | 166,306.00 | — | 274,399.33 |
| RLU (1,000-0) | 159,745.67 | 165,901.33 | — | 273,916.00 |

TABLE 24

| [IL-18] | Calibrator Signal (RLU) | | | | |
|---|---|---|---|---|---|
| pg/mL | E | F | G | H | I |
| 0 | 545.33 | 545.33 | 545.33 | 545.33 | 545.33 |
| 25 | 4,888.00 | 4,403.67 | 7,446.67 | 8,311.00 | 8,296.00 |
| 75 | 14,314.33 | 10,598.67 | 21,070.00 | 23,786.00 | 23,221.67 |
| 250 | 46,383.00 | 34,629.67 | 69,254.67 | 76,460.33 | 73,876.33 |
| 600 | 111,701.00 | 81,116.67 | 160,471.00 | 180,563.00 | 174,062.33 |
| 1,000 | 177,084.67 | 140,186.67 | 261,769.67 | 282,829.33 | 279,198.33 |
| RLU (1,000-0) | 176,539.33 | 139,641.33 | 261,224.33 | 282,284.00 | 278,653.00 |

The mean RLU differential between day 0 and day 31 at about 2° C. to about 8° C. was −6.26 for calibrator A, −2.87 for calibrator B, 5.95 for calibrator D, 0.34 for calibrator E, −4.46 for calibrator F, −7.31 for calibrator G, −5.54 for calibrator H, and −4.98 for calibrator I. Thus, unalkylated IL-18 in the presence of 1% or 5% BSA and alkylated IL-18 in the presence of 1% BSA remained relatively stable at about 2° C. to about 8° C. over 31 days.

Example 8

This example compares the stability of calibrating compositions comprising various IL-18s in the presence of 1% BSA at about 2° C. to about 8° C. and at about 37° C.

The chemiluminescent microparticle immunoassay described in Example 6 was used in the comparison.

At day 0, the data were as follows in Tables 25 and 26:

TABLE 25

| [IL-18] | Calibrator Signal (RLU) | | | | |
|---|---|---|---|---|---|
| pg/mL | A | B | C | D | E |
| 0 | 431.60 | 431.60 | 431.60 | 431.60 | 431.60 |
| 25 | 6,007.00 | 4,376.25 | 6,922.00 | 4,388.00 | 5,662.00 |
| 75 | 16,436.50 | 11,901.25 | 20,107.00 | 12,060.25 | 16,421.50 |
| 250 | 55,712.75 | 38,721.25 | 67,134.00 | 40,666.75 | 53,102.50 |
| 600 | 127,158.00 | 89,877.50 | 155,447.50 | 92,662.25 | 124,561.25 |
| 1,000 | 208,096.25 | 146,654.50 | 259,734.00 | 154,627.75 | 204,440.50 |
| RLU (1,000-0) | 207,664.65 | 146,222.90 | 259,302.40 | 154,196.15 | 204,008.90 | wherein calibrators A-D comprise different lots of rhIL-18 from Abbott Laboratories (calibrator A; GST-Pro-FXa-IL18=BT 132547) and MBL (calibrators B-D) and alkylated rhIL-18 (calibrator E). The calibrator diluent contained 1% BSA, 35 mM phosphate, 150 mM NaCl, and 0.1% azide, pH 6.

TABLE 26

| [IL-18] | Calibrator Signal (RLU) | | | |
|---|---|---|---|---|
| pg/mL | F | G | H | I |
| 0 | 431.60 | 431.60 | 431.60 | 431.60 |
| 25 | 5,925.75 | 6,578.75 | 2,247.00 | 3,636.75 |
| 75 | 16,569.00 | 18,443.00 | 5,840.00 | 9,870.75 |
| 250 | 53,635.25 | 59,142.25 | 19,531.25 | 32,687.00 |
| 600 | 127,476.50 | 138,937.00 | 44,556.75 | 77,205.00 |
| 1,000 | 206,578.00 | 224,175.50 | 73,273.00 | 124,612.75 |
| RLU (1,000-0) | 206,146.40 | 223,743.90 | 72,841.40 | 124,181.15 | wherein calibrators F-I comprise different lots of rhIL-18 from MBL (calibrator H was stored at 2-8° C., instead of −70° C., so it was degraded at Day 0) and Abbott Laboratories (calibrator I; Abbott GST-Pro-FXa-IL18=BT Lot 132525).

At day 7 at about 37° C., the data were as follows in Tables 27 and 28:

TABLE 27

| [IL-18] pg/mL | Calibrator Signal (RLU) | | | | |
|---|---|---|---|---|---|
| | A | B | C | D | E |
| 0 | 470.00 | 470.00 | 470.00 | 470.00 | 470.00 |
| 25 | 5,575.33 | 3,825.67 | 6,302.33 | 1,404.00 | 5,602.00 |
| 75 | 15,182.00 | 10,269.00 | 17,770.00 | 3,033.00 | 15,279.00 |
| 250 | 49,475.00 | 34,485.67 | 59,874.00 | 8,686.33 | 51,196.67 |
| 600 | 104,768.67 | 78,483.67 | 126,026.67 | 19,158.33 | 113,311.00 |
| 1,000 | 146,934.67 | 121,687.67 | 189,743.67 | 31,138.33 | 188,814.67 |
| RLU (1,000-0) | 146,464.67 | 121,217.67 | 189,273.67 | 30,668.33 | 188,344.67 |

TABLE 28

| [IL-18] pg/mL | Calibrator Signal (RLU) | | | |
|---|---|---|---|---|
| | F | G | H | I |
| 0 | 470.00 | 470.00 | 470.00 | 470.00 |
| 25 | 5,291.33 | 5,919.67 | 2,150.00 | 3,170.00 |
| 75 | 15,019.67 | 15,674.00 | 5,480.00 | 7,713.00 |
| 250 | 46,394.00 | 51,271.33 | 18,050.67 | 24.973.33 |
| 600 | 104,593.33 | 111,336.67 | 39,963.33 | 55,466.67 |
| 1,000 | 159,704.00 | 163,976.67 | 69,383.33 | 84,741.33 |
| RLU (1,000-0) | 159,234.00 | 163,506.67 | 68,913.33 | 84,271.33 |

The mean RLU differential between day 0 and day 7 at about 37° C. was −14.60 for calibrator A, −13.39 for calibrator B, −15.45 for calibrator C, −76.14 for calibrator D, −5.66 for calibrator E, −14.84 for calibrator F, −17.01 for calibrator G, −6.74 for calibrator H, and −23.69 for calibrator I. Thus, alkylated rhIL-18 was more stable than the unalkylated rhIL-18s in the presence of 1% BSA at about 37° C. for seven days.

At day 7 at about 2° C. to about 8° C., the data were as follows in Tables 29 and 30:

TABLE 29

| [IL-18] pg/mL | Calibrator Signal (RLU) | | | | |
|---|---|---|---|---|---|
| | A | B | C | D | E |
| 0 | 446.00 | 446.00 | 446.00 | 446.00 | 446.00 |
| 25 | 5,779.33 | 4,350.33 | 6,912.67 | 4,425.00 | 6,010.67 |
| 75 | 16,902.00 | 11,692.00 | 19,291.33 | 11,852.67 | 16,919.00 |
| 250 | 56,613.00 | 39,544.00 | 68,890.33 | 40,106.67 | 54,342.33 |
| 600 | 124,360.00 | 91,101.67 | 154,213.33 | 93,844.00 | 123,885.67 |
| 1,000 | 210,012.00 | 144,151.33 | 248,418.00 | 154,865.67 | 202,019.00 |
| RLU (1,000-0) | 209,566.00 | 143,705.33 | 247,972.00 | 154,419.67 | 201,573.00 |

TABLE 30

| [IL-18] pg/mL | Calibrator Signal (RLU) | | | |
|---|---|---|---|---|
| | F | G | H | I |
| 0 | 446.00 | 446.00 | 446.00 | 446.00 |
| 25 | 5,695.67 | 6,520.00 | 2,297.67 | 3,861.33 |
| 75 | 16,796.67 | 18,643.00 | 6,137.00 | 10,217.33 |
| 250 | 53,346.00 | 58,223.33 | 18,876.00 | 33,640.67 |
| 600 | 127,178.00 | 136,504.00 | 44,402.33 | 77,534.67 |
| 1,000 | 206,579.00 | 219,086.00 | 72,092.67 | 125,525.00 |
| RLU (1,000-0) | 206,133.00 | 218,640.00 | 71,646.67 | 125,079.00 |

The mean RLU differential between day 0 and day 7 at about 2° C. to about 8° C. was −0.12 for calibrator A, −0.11 for calibrator B, −1.35 for calibrator C, −0.17 for calibrator D, 1.96 for calibrator E, −0.66 for calibrator F, −1.08 for calibrator G, 0.41 for calibrator H, and 2.75 for calibrator I. Thus, alkylated and unalkylated rhIL-18s in the presence of 1% BSA were relatively stable at about 2° C. to about 8° C. for seven days.

At day 21 at about 37° C., the data were as follows in Tables 31 and 32:

TABLE 31

| [IL-18] pg/mL | Calibrator Signal (RLU) | | | | |
|---|---|---|---|---|---|
| | A | B | C | D | E |
| 0 | 420.50 | 420.50 | 420.50 | 420.50 | 420.50 |
| 25 | 4,537.33 | 3,001.00 | 5,092.00 | 956.33 | 5,084.00 |
| 75 | 11,876.00 | 8,400.33 | 13,888.67 | 2,002.33 | 13,986.67 |
| 250 | 36,858.33 | 26,949.67 | 46,111.00 | 6,055.00 | 44,991.33 |
| 600 | 75,155.33 | 59,577.67 | 96,049.67 | 13,606.67 | 103,832.33 |
| 1,000 | 103,560.67 | 92,251.33 | 137,644.67 | 21,486.67 | 172,868.67 |
| RLU (1,000-0) | 103,140.17 | 91,830.83 | 137,224.17 | 21,066.17 | 172,448.17 |

TABLE 32

| [IL-18] pg/mL | Calibrator Signal (RLU) | | | |
|---|---|---|---|---|
| | F | G | H | I |
| 0 | 420.50 | 420.50 | 420.50 | 420.50 |
| 25 | 4,179.00 | 4,536.00 | 2,071.67 | 2,269.67 |
| 75 | 11,444.67 | 12,256.67 | 4,514.50 | 5,604.67 |
| 250 | 34,912.33 | 38,148.33 | 15,029.33 | 18,698.33 |
| 600 | 77,599.67 | 79,559.67 | 34,626.00 | 39,764.67 |
| 1,000 | 114,298.33 | 114,410.33 | 56,012.67 | 60,384.00 |
| RLU (1,000-0) | 113,877.83 | 113,989.83 | 55,592.17 | 59,963.50 |

The mean RLU differential between day 0 and day 21 at about 37° C. was −35.44 for calibrator A, −32.41 for calibrator B, −34.78 for calibrator C, −83.63 for calibrator D, −14.48 for calibrator E, −35.82 for calibrator F, −38.36 for calibrator G, −19.88 for calibrator H, and −44.73 for calibrator I. Thus, alkylated rhIL-18 was more stable than the unalkylated rhIL-18s in the presence of 1% BSA at about 37° C. for 21 days.

At day 21 at about 2° C. to about 8° C., the data were as follows in Tables 33 and 34:

TABLE 33

| [IL-18] pg/mL | Calibrator Signal (RLU) | | | | |
|---|---|---|---|---|---|
| | A | B | C | D | E |
| 0 | 479.00 | 479.00 | 479.00 | 479.00 | 479.00 |
| 25 | 6,021.00 | 4,121.67 | 7,098.33 | 4,289.67 | 5,558.67 |
| 75 | 17,136.00 | 11,582.00 | 18,368.33 | 11,978.67 | 16,269.67 |
| 250 | 55,304.00 | 38,697.33 | 64,965.33 | 40,088.33 | 51,460.00 |
| 600 | 123,101.00 | 87,288.00 | 144,331.67 | 90,111.00 | 121,943.00 |
| 1,000 | 197,109.00 | 141,606.33 | 241,073.33 | 146,742.67 | 197,574.00 |
| RLU (1,000-0) | 196,630.00 | 141,127.33 | 240,594.33 | 146,263.67 | 197,095.00 |

TABLE 34

| [IL-18] pg/mL | Calibrator Signal (RLU) | | | |
|---|---|---|---|---|
| | F | G | H | I |
| 0 | 479.00 | 479.00 | 479.00 | 479.00 |
| 25 | 5,803.00 | 6,037.33 | 2,525.33 | 3,721.00 |
| 75 | 16,235.00 | 16,998.00 | 5,608.33 | 10,079.33 |
| 250 | 51,268.00 | 56,451.00 | 18,661.33 | 33,082.00 |
| 600 | 121,301.33 | 130,118.00 | 42,680.00 | 74,741.00 |
| 1,000 | 201,586.00 | 217,338.33 | 71,939.00 | 121,463.67 |
| RLU (1,000-0) | 201,107.00 | 216,859.33 | 71,460.00 | 120,984.67 |

The mean RLU differential between day 0 and day 21 at about 2° C. to about 8° C. was −0.94 for calibrator A, −2.98 for calibrator B, −4.73 for calibrator C, −2.44 for calibrator D, −2.26 for calibrator E, −3.15 for calibrator F, −6.00 for calibrator G, −0.41 for calibrator H, and −0.02 for calibrator I. Thus, alkylated and unalkylated rhIL-18s in the presence of 1% BSA were stable at about 2° C. to about 8° C. for 21 days.

At day 31 at about 37° C., the data were as follows in Tables 35 and 36:

TABLE 35

| [IL-18] pg/mL | Calibrator Signal (RLU) | | | | |
|---|---|---|---|---|---|
| | A | B | C | D | E |
| 0 | 471.00 | 471.00 | 471.00 | 471.00 | 471.00 |
| 25 | 3,654.00 | 3,050.00 | 4,682.50 | 1,064.50 | 5,023.50 |
| 75 | 10,131.00 | 7,563.00 | 12,436.50 | 2,241.00 | 14,044.50 |
| 250 | 31,746.50 | 23,847.00 | 41,737.50 | 5,412.50 | 45,103.00 |
| 600 | 64,830.00 | 53,897.50 | 87,192.50 | 13,165.00 | 102,656.00 |
| 1,000 | 89,214.00 | 80,434.00 | 125,058.00 | 20,383.50 | 166,174.00 |
| RLU (1,000-0) | 88,743.00 | 79,963.00 | 124,587.00 | 19,912.50 | 165,703.00 |

TABLE 36

| [IL-18] pg/mL | Calibrator Signal (RLU) | | | |
|---|---|---|---|---|
| | F | G | H | I |
| 0 | 471.00 | 471.00 | 471.00 | 471.00 |
| 25 | 3,979.00 | 4,161.00 | 2,101.00 | 2,310.00 |
| 75 | 10,295.50 | 10,415.00 | 4,465.50 | 5,282.50 |
| 250 | 31,741.00 | 34,348.00 | 14,406.50 | 16,078.50 |
| 600 | 69,400.00 | 72,540.00 | 32,996.00 | 33,316.00 |
| 1,000 | 99,626.00 | 102,969.50 | 53,035.50 | 51,328.50 |
| RLU (1,000-0) | 99,155.00 | 102,498.50 | 52,564.50 | 50,857.50 |

The mean RLU differential between day 0 and day 31 at about 37° C. was −45.34 for calibrator A, −38.07 for calibrator B, −40.82 for calibrator C, −83.29 for calibrator D, −15.42 for calibrator E, −41.77 for calibrator F, −44.81 for calibrator G, −21.97 for calibrator H, and −49.89 for calibrator I. Thus, alkylated rhIL-18 was more stable than the unalkylated rhIL-18s in the presence of 1% BSA at about 37° C. for 31 days.

At day 31 at about 2° C. to about 8° C., the data were as follows in Table 37:

TABLE 37

| [IL-18] | Calibrator Signal (RLU) | | | | | |
|---|---|---|---|---|---|---|
| pg/mL | A | B | C | E | F | G |
| 0 | 603.00 | 603.00 | 603.00 | 603.00 | 603.00 | 603.00 |
| 25 | 5,901.50 | 4,727.00 | 7,584.00 | 5,560.00 | 6,150.50 | 6,148.00 |
| 75 | 17,183.50 | 11,510.00 | 19,686.00 | 15,491.50 | 16,432.00 | 19,034.00 |
| 250 | 55,286.00 | 37,353.50 | 66,069.00 | 52,451.50 | 51,154.50 | 58,085.50 |
| 600 | 121,104.50 | 88,368.50 | 154,334.50 | 124,859.50 | 121,716.50 | 129,965.50 |
| 1,000 | 202,664.00 | 146,934.50 | 246,463.50 | 196,236.50 | 195,910.50 | 208,146.00 |
| RLU (1,000-0) | 202,061.00 | 146,331.50 | 245,860.50 | 195,633.50 | 195,307.50 | 207,543.00 |

The mean RLU differential between day 0 and day 31 at about 2° C. to about 8° C. was −1.07 for calibrator A, −0.06 for calibrator B, 0.01 for calibrator C, −2.49 for calibrator E, −2.27 for calibrator F, and −3.75 for calibrator G. Thus, alkylated and unalkylated rhIL-18s were stable at about 2° C. to about 8° C. for 31 days.

Example 9

This example compares the stability of calibrating compositions comprising various IL-18s in the presence of 1% BSA at about 2° C. to about 8° C. and at about 37° C.

The chemiluminescent microparticle immunoassay described in Example 6 was used in the comparison.

At day 0, the data were as follows in Table 38:

TABLE 38

| [IL-18] | Calibrator Signal (RLU) | |
|---|---|---|
| pg/mL | A | B |
| 0 | 396.33 | 396.33 |
| 25 | 6,843.00 | 4,259.00 |
| 75 | 19,018.67 | 12,534.33 |
| 250 | 63,116.33 | 40,502.33 |
| 600 | 142,541.00 | 96,795.67 |
| 1,000 | 228,318.00 | 152,966.67 |
| RLU (1,000-0) | 227,921.67 | 152,570.33 | wherein calibrator A comprises rhIL-18 from MBL and calibrator B comprises alkylated rhIL-18. The calibrator diluent contained 1% BSA, 35 mM phosphate, 150 mM NaCl, and 0.1% azide, pH 5.8.

At day 7 at about 37° C., the data were as follows in Table 39:

TABLE 39

| [IL-18] | Calibrator Signal (RLU) | |
|---|---|---|
| pg/mL | A | B |
| 0 | 297.00 | 297.00 |
| 25 | 6,025.00 | 4,232.33 |

TABLE 39-continued

| [IL-18] | Calibrator Signal (RLU) | |
|---|---|---|
| pg/mL | A | B |
| 75 | 16,773.33 | 11,801.33 |
| 250 | 57,908.33 | 39,569.33 |
| 600 | 126,164.67 | 91,536.33 |
| 1,000 | 196,386.00 | 149,628.33 |
| RLU (1,000-0) | 196,089.00 | 149,331.33 |

The mean RLU differential between day 0 and day 7 at about 37° C. was −11.50 for calibrator A and −3.28 for calibrator B. Thus, alkylated rhIL-18 was relatively stable over seven days and was more stable than unalkylated rhIL-18.

At day 7 at about 2° C. to about 8° C., the data were as follows in Table 40:

TABLE 40

| [IL-18] | Calibrator Signal (RLU) | |
|---|---|---|
| pg/mL | A | B |
| 0 | 513.33 | 513.33 |
| 25 | 6,746.00 | 4,271.00 |
| 75 | 19,095.00 | 12,245.67 |
| 250 | 62,954.67 | 40,366.00 |
| 600 | 146,183.33 | 94,554.33 |
| 1,000 | 235,339.33 | 152,360.33 |
| RLU (1,000-0) | 234,826.00 | 151,847.00 |

The mean RLU differential between day 0 and day 7 at about 2° C. to about 8° C. was 0.87 for calibrator A, and −1.01 for calibrator B. Thus, alkylated and unalkylated rhIL-18s were each relatively stable at about 2° C. to about 8° C. for seven days.

At day 21 at about 37° C., the data were as follows in Table 41:

TABLE 41

| [IL-18] pg/mL | Calibrator Signal (RLU) | |
|---|---|---|
| | A | B |
| 0 | 299.00 | 299.00 |
| 25 | 5,083.67 | 4,063.67 |
| 75 | 13,957.00 | 11,039.33 |
| 250 | 44,470.67 | 37,584.33 |
| 600 | 101,150.67 | 87,255.33 |
| 1,000 | 155,385.33 | 137,850.00 |
| RLU (1,000-0) | 155,086.33 | 137,551.00 |

The mean RLU differential between day 0 and day 21 at about 37° C. was −28.57 for calibrator A, and −8.69 for calibrator B. Thus, alkylated rhIL-18 was relatively stable at about 37° C. for 21 days and was more stable than unalkylated rhIL-18.

At day 21 at about 2° C. to about 8° C., the data were as follows in Table 42:

TABLE 42

| [IL-18] pg/mL | Calibrator Signal (RLU) | |
|---|---|---|
| | A | B |
| 0 | 284.00 | 284.00 |
| 25 | 6,829.00 | 4,415.67 |
| 75 | 19,815.00 | 12,331.00 |
| 250 | 64,792.33 | 42,044.00 |
| 600 | 145,111.67 | 95,786.33 |
| 1,000 | 237,062.67 | 154,750.67 |
| RLU (1,000-0) | 236,778.67 | 154,466.67 |

The mean RLU differential between day 0 and day 21 at about 2° C. to about 8° C. was 2.45 for calibrator A, and 1.20 for calibrator B. Thus, alkylated and unalkylated rhIL-18 were each relatively stable at 2° C. to about 8° C. for 21 days.

At day 30 at about 37° C., the data were as follows in Table 43:

TABLE 43

| [IL-18] pg/mL | Calibrator Signal (RLU) | |
|---|---|---|
| | A | B |
| 0 | 426.67 | 426.67 |
| 25 | 4,615.33 | 3,722.67 |
| 75 | 12,394.67 | 11,218.67 |
| 250 | 42,558.00 | 36,941.00 |
| 600 | 90,462.33 | 85,008.33 |
| 1,000 | 135,789.00 | 136,284.00 |
| RLU (1,000-0) | 135,362.33 | 135,857.33 |

The mean RLU differential between day 0 and day 30 at about 37° C. was −35.40 for calibrator A, and −10.99 for calibrator B. Thus, alkylated rhIL-18 was relatively stable at about 37° C. for 30 days and was more stable than unalkylated rhIL-18.

At day 30 at about 2° C. to about 8° C., the data were as follows in Table 44:

TABLE 44

| [IL-18] pg/mL | Calibrator Signal (RLU) | |
|---|---|---|
| | A | B |
| 0 | 299.33 | 299.33 |
| 25 | 6,906.00 | 4,535.00 |
| 75 | 20,015.67 | 12,946.00 |
| 250 | 66,436.33 | 42,251.00 |
| 600 | 149,673.33 | 98,371.33 |
| 1,000 | 245,421.67 | 160,328.67 |
| RLU (1,000-0) | 245,122.33 | 160,029.33 |

The mean RLU differential between day 0 and day 3 at about 2° C. to about 8° C. was 4.78 for calibrator A, and 4.10 for calibrator B. Thus, alkylated and unalkylated rhIL-18s were each relatively stable at about 2° C. to about 8° C. for 30 days.

These results thus confirm and are consistent with those in Example 8.

Example 10

This example compares the stability of calibrating compositions comprising unalkylated IL-18 versus alkylated IL-18 in the presence of 1% BSA at about 2° C. to about 8° C. and at about 37° C.

The chemiluminescent microparticle immunoassay described in Example 5 was used in the comparison.

At day 0, the data were as follows in Table 45:

TABLE 45

| [IL-18] pg/mL | Calibrator Signal (RLU) | | |
|---|---|---|---|
| | A | B | C |
| 0 | 855.00 | 855.00 | 855.00 |
| 25 | 11,876.33 | 20,279.33 | 16,628.33 |
| 75 | 31,072.67 | 58,986.00 | 47,670.67 |
| 250 | 100,818.33 | 188,629.33 | 151,909.67 |
| 600 | 236,894.00 | 428,786.33 | 352,698.00 |
| 1,000 | 396,497.67 | 699,042.33 | 592,806.00 |
| RLU (1,000-0) | 395,642.67 | 698,187.33 | 591,951.00 | wherein calibrator A=unalkylated (native) IL-18, calibrator B=IL-18 alkylated with iodoacetamide, calibrator C=IL-18 alkylated with iodoacetic acid. The calibrator diluent contained 35 mM phosphate, 150 mM NaCl, 1% BSA, and 0.1% azide, pH 6.

At day 7 at about 37° C., the data were as follows in Table 46:

TABLE 46

| [IL-18] pg/mL | Calibrator Signal (RLU) | | |
|---|---|---|---|
| | A | B | C |
| 0 | 667.50 | 667.50 | 667.50 |
| 25 | 5,860.67 | 18,035.33 | 13,275.67 |
| 75 | 15,109.67 | 53,345.33 | 37,391.00 |
| 250 | 46,850.67 | 168,960.33 | 120,379.33 |
| 600 | 104,613.67 | 376,696.33 | 256,457.67 |
| 1,000 | 153,379.00 | 583,871.00 | 396,751.00 |
| RLU (1,000-0) | 152,711.50 | 583,203.50 | 396,083.50 |

The mean RLU differential between day 0 and day 7 at about 37° C. was −54.54 for calibrator A, −11.94 for calibrator B, and −24.57 for calibrator C. Thus, both alkylated rhIL-18s showed better stability than the unalkylated (native) IL-18 at 37° C. over seven days.

At day 7 at about 2-8° C., the data were as follows in Table 47:

TABLE 47

| [IL-18] pg/mL | Calibrator Signal (RLU) | | |
|---|---|---|---|
| | A | B | C |
| 0 | 743.00 | 743.00 | 743.00 |
| 25 | 10,877.67 | 19,483.67 | 16,550.33 |
| 75 | 29,073.33 | 57,031.00 | 45,119.33 |
| 250 | 93,747.67 | 185,058.33 | 147,531.33 |
| 600 | 210,633.00 | 403,541.00 | 330,872.67 |
| 1,000 | 365,155.33 | 667,333.67 | 552,992.00 |
| RLU (1,000-0) | 364,412.33 | 666,590.67 | 552,249.00 |

The mean RLU differential between day 0 and day 7 at about 2-8° C. was −8.17 for calibrator A, −3.91 for calibrator B, and −4.32 for calibrator C. Thus, both alkylated rhIL-18s showed better stability than the unalkylated (native) IL-18 at 37° C. over seven days. The iodoacetamide alkylation, however, yielded an alkylated IL-18 with a higher capping ratio, which improved stability at 37° C.

At day 7 at about 2° C. to about 8° C., the data were as follows in Table 48:

TABLE 48

| [IL-18] pg/mL | Calibrator Signal (RLU) | | |
|---|---|---|---|
| | A | B | C |
| 0 | 513.33 | 513.33 | 513.33 |
| 25 | 6,746.00 | 4,271.00 | 11,038.00 |
| 75 | 19,095.00 | 12,245.67 | 31,227.00 |
| 250 | 62,954.67 | 40,366.00 | 101,093.67 |
| 600 | 146,183.33 | 94,554.33 | 229,439.67 |
| 1,000 | 235,339.33 | 152,360.33 | 363,061.33 |
| RLU (1,000-0) | 234,826.00 | 151,847.00 | 362,548.00 |

The mean RLU differential between day 0 and day 7 at about 2° C. to about 8° C. was 0.87 for calibrator A, −1.01 for calibrator B, and 0.47 for calibrator C. Thus, alkylated and unalkylated rhIL-18s were all relatively stable at about 2° C. to about 8° C. for 7 days as observed in the previous examples.

Example 11

This example compares the stability of calibrating compositions comprising two different lots of unalkylated IL-18 versus the same two lots of IL-18 alkylated with iodoacetamide in the presence of 1% BSA at about 2° C. to about 8° C. and at about 37° C.

The chemiluminescent microparticle immunoassay described in Example 5 was used in the comparison.

At day 0, the data were as follows in Table 49:

TABLE 49

| [IL-18] pg/mL | Calibrator Signal (RLU) | | | |
|---|---|---|---|---|
| | A | B | C | D |
| 0 | 488.00 | 488.00 | 488.00 | 488.00 |
| 25 | 7469.00 | 12713.67 | 6873.00 | 7263.67 |
| 75 | 21810.00 | 37309.67 | 20226.67 | 20658.67 |
| 250 | 72071.67 | 122521.67 | 66127.67 | 66539.50 |

TABLE 49-continued

| [IL-18] pg/mL | Calibrator Signal (RLU) | | | |
|---|---|---|---|---|
| | A | B | C | D |
| 600 | 163229.67 | 280391.00 | 151322.67 | 158354.00 |
| 1,000 | 264984.33 | 458456.67 | 239256.00 | 250012.33 |
| RLU (1,000-0) | 264,496.33 | 457,968.67 | 238,768.00 | 249,524.33 | wherein calibrator A=unalkylated (native) IL-18, calibrator B=IL-18 alkylated with iodoacetamide, calibrator C=unalkylated (native) IL-18, calibrator D=IL-18 alkylated with iodoacetamide. The calibrator diluent contained 35 mM phosphate, 150 mM NaCl, 1% BSA, and 0.1% azide, pH 6.

At day 7 at about 37° C., the data were as follows in Table 50:

TABLE 50

| [IL-18] pg/mL | Calibrator Signal (RLU) | | | |
|---|---|---|---|---|
| | A | B | C | D |
| 0 | 497.33 | 497.33 | 497.33 | 497.33 |
| 25 | 6,562.00 | 13,339.67 | 6,359.67 | 6,923.00 |
| 75 | 19,968.33 | 38,260.00 | 17,880.33 | 20,751.00 |
| 250 | 65,635.67 | 122,797.67 | 60,126.33 | 66,384.00 |
| 600 | 145,509.33 | 273,361.33 | 134,140.67 | 153,584.00 |
| 1,000 | 226,133.67 | 436,595.67 | 212,688.33 | 237,949.33 |
| RLU (1,000-0) | 225,636.33 | 436,098.33 | 212,191.00 | 237,452.00 |

The mean RLU differential between day 0 and day 7 at about 37° C. was −11.01 for calibrator A, 0.08 for calibrator B, −10.12 for calibrator C, and −2.46 for calibrator D. Thus, alkylated rhIL-18 was more stable than the unalkylated rhIL-18s in the presence of 1% BSA at about 37° C. for seven days.

At day 7 at about 2-8° C., the data were as follows in Table 51:

TABLE 51

| [IL-18] pg/mL | Calibrator Signal (RLU) | | | |
|---|---|---|---|---|
| | A | B | C | D |
| 0 | 413.67 | 413.67 | 413.67 | 413.67 |
| 25 | 7,634.67 | 13,142.00 | 7,127.33 | 7,489.33 |
| 75 | 21,774.67 | 38,379.67 | 19,852.33 | 20,251.33 |
| 250 | 71,521.67 | 125,577.33 | 66,542.33 | 67,647.00 |
| 600 | 165,858.00 | 278,492.00 | 150,921.67 | 153,427.67 |
| 1,000 | 258,354.67 | 441,979.00 | 242,440.33 | 248,559.67 |
| RLU (1,000-0) | 257,941.00 | 441,565.33 | 242,026.67 | 248,146.00 |

The mean RLU differential between day 0 and day 7 at about 2° C. to about 8° C. was −0.08 for calibrator A, 0.89 for calibrator B, 0.71 for calibrator C, and −0.18 for calibrator D. Thus, alkylated and unalkylated rhIL-18s in the presence of 1% BSA were stable at about 2° C. to about 8° C. for 7 days.

At day 30 at about 37° C., the data were as follows in Table 52:

TABLE 52

| [IL-18] pg/mL | Calibrator Signal (RLU) | | | |
|---|---|---|---|---|
| | A | B | C | D |
| 0 | 391.33 | 391.33 | 391.33 | 391.33 |
| 25 | 5,090.33 | 12,159.67 | 4,772.33 | 7,084.00 |
| 75 | 14,347.67 | 33,905.67 | 13,698.33 | 19,963.33 |

TABLE 52-continued

| [IL-18] | Calibrator Signal (RLU) | | | |
|---|---|---|---|---|
| pg/mL | A | B | C | D |
| 250 | 46,144.33 | 110,936.67 | 43,941.00 | 64,208.67 |
| 600 | 99,579.33 | 255,803.00 | 94,457.00 | 156,842.00 |
| 1,000 | 151,980.33 | 401,925.00 | 146,578.67 | 250,198.67 |
| RLU (1,000-0) | 151,589.00 | 401,533.67 | 146,187.33 | 249,807.33 |

The mean RLU differential between day 0 and day 30 at about 37° C. was −36.74 for calibrator A, −8.81 for calibrator B, −34.54 for calibrator C, and −2.04 for calibrator D. Thus, alkylated rhIL-18 was more stable than the unalkylated rhIL-18s in the presence of 1% BSA at about 37° C. for 30 days.

At day 30 at about 2-8° C., the data were as follows in Table 53:

TABLE 53

| [IL-18] | Calibrator Signal (RLU) | | | |
|---|---|---|---|---|
| pg/mL | A | B | C | D |
| 0 | 519.00 | 519.00 | 519.00 | 519.00 |
| 25 | 7,916.33 | 13,403.00 | 7,350.00 | 7,229.33 |
| 75 | 22,248.00 | 39,916.67 | 21,287.33 | 21,840.67 |
| 250 | 75,630.67 | 132,004.33 | 67,609.00 | 70,668.67 |
| 600 | 170,335.67 | 284,926.67 | 156,160.67 | 164,637.00 |
| 1,000 | 268,887.00 | 453,723.67 | 250,389.33 | 253,362.67 |
| RLU (1,000-0) | 268,368.00 | 453,204.67 | 249,870.33 | 252,843.67 |

The mean RLU differential between day 0 and day 30 at about 2° C. to about 8° C. was −3.75 for calibrator A, 4.15 for calibrator B, 4.45 for calibrator C, and 3.35 for calibrator D. Thus, alkylated and unalkylated rhIL-18s in the presence of 1% BSA were stable at about 2° C. to about 8° C. for 30 days.

All patents, patent application publications, journal articles, textbooks, and other publications mentioned in the specification are indicative of the level of skill of those in the art to which the invention pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. A composition comprising (i) an isolated or purified, alkylated IL-18, in which at least one free sulfhydryl of a cysteine residue has been alkylated, and (ii) at least one stabilizing protein.

2. The composition of claim 1, in which the hydrogen of at least one free sulfhydryl of a cysteine residue has been replaced with carboxyamidomethyl, and, optionally, in which the protein is bovine serum albumin (BSA).

3. The composition of claim 2, in which the alkylated IL-18 has a capping ratio of about 2.5 to about 4.0 as determined by mass spectrometry, and, optionally, in which the protein is BSA.

4. The composition of claim 1, in which the hydrogen of at least one free sulfhydryl of a cysteine residue has been replaced with carboxymethyl, and, optionally, in which the protein is BSA.

5. The composition of claim 4, in which the alkylated IL-18 has a capping ratio of about 1.0 to about 4.0 as determined by mass spectrometry, and, optionally, in which the protein is BSA.

6. The composition of claim 1, in which the protein is selected from the group consisting of BSA, human serum albumin (HSA), bovine γ-globulin (BGG), Carnation® Instant Nonfat Dry Milk, and any combination thereof.

7. The composition of claim 1, in which the protein is BSA.

8. The composition of claim 1, which comprises a known concentration of alkylated IL-18.

9. A series of calibrating compositions, which can be used in a method of determining the concentration of IL-18 in a sample, wherein each of the compositions in the series comprises (i) a known concentration of an isolated or purified, alkylated IL-18, in which at least one free sulfhydryl of a cysteine residue has been alkylated, and (ii) at least one stabilizing protein, wherein each of the compositions differs from the other compositions in the series by the concentration of alkylated IL-18.

10. The series of calibrating compositions of claim 9, in which the hydrogen of at least one free sulfhydryl of a cysteine residue has been replaced with carboxyamidomethyl, and, optionally, in which the protein is BSA.

11. The series of calibrating compositions of claim 10, in which the alkylated IL-18 has a capping ratio of about 2.5 to about 4.0 as determined by mass spectrometry, and, optionally, in which the protein is BSA.

12. The series of calibrating compositions of claim 9, in which the hydrogen of at least one free sulfhydryl of a cysteine residue has been replaced with carboxymethyl, and, optionally, in which the protein is BSA.

13. The series of calibrating compositions of claim 12, in which the alkylated IL-18 has a capping ratio of about 1.0 to about 4.0 as determined by mass spectrometry, and, optionally, in which the protein is BSA.

14. The series of calibrating compositions of claim 9, in which the protein is selected from the group consisting of BSA, HSA, BGG, Carnation® Instant Nonfat Dry Milk, and any combination thereof.

15. The series of calibrating compositions of claim 9, in which the protein is BSA.

16. A kit for assaying a test sample for IL-18, which kit comprises at least one component for assaying the test sample for IL-18 and instructions for assaying the test sample for IL-18, wherein the at least one component includes at least one composition comprising (i) a known amount of an isolated or purified, alkylated IL-18, in which at least one free sulfhydryl of a cysteine residue has been alkylated, and (ii) at least one stabilizing protein, wherein, if the kit comprises more than one composition, each of the compositions differs from the other compositions by the concentration of alkylated IL-18.

\* \* \* \* \*